US012004846B2

(12) United States Patent
Bobo et al.

(10) Patent No.: US 12,004,846 B2
(45) Date of Patent: Jun. 11, 2024

(54) NON-INVASIVE SYSTEMS AND METHODS FOR THE IMPROVED EVALUATION OF PATIENTS SUFFERING FROM UNDIAGNOSED HEADACHES

(71) Applicant: Cerenetex, Inc., Newport Beach, CA (US)

(72) Inventors: Benjamin William Bobo, Irvine, CA (US); Mohsin Shah, Tustin, CA (US); John Chen, Tustin, CA (US); Michael Horowitz, Naples, FL (US); Timothy Hays, La Jolla, CA (US)

(73) Assignee: Cerenetex, Inc., Newport Beach, CA (US)

( * ) Notice: Subject to any disclaimer, the term of this patent is extended or adjusted under 35 U.S.C. 154(b) by 0 days.

(21) Appl. No.: 17/226,372

(22) Filed: Apr. 9, 2021

(65) Prior Publication Data

US 2021/0321880 A1 Oct. 21, 2021

Related U.S. Application Data

(63) Continuation-in-part of application No. 16/380,841, filed on Apr. 10, 2019, now Pat. No. 11,076,797.
(Continued)

(51) Int. Cl.
*A61B 5/00* (2006.01)
*A61B 5/026* (2006.01)

(52) U.S. Cl.
CPC ............ *A61B 5/026* (2013.01); *A61B 5/6803* (2013.01); *A61B 5/743* (2013.01); *A61B 2562/0204* (2013.01)

(58) Field of Classification Search
CPC ..... A61B 5/4064; A61B 5/026; A61B 5/1102; A61B 5/6803; A61B 5/4082;
(Continued)

(56) References Cited

U.S. PATENT DOCUMENTS 4,008,711 A 2/1977 Olinger
5,492,129 A 2/1996 Greenberger
(Continued)

FOREIGN PATENT DOCUMENTS

AT 495791 T 2/2011
AT 527016 T 10/2011
(Continued)

OTHER PUBLICATIONS

Written Opinion of the International Searching Authority for PCT/US19/26833, Sep. 13, 2019.
(Continued)

*Primary Examiner* — Carl H Layno
*Assistant Examiner* — Anh-Khoa N Dinh
(74) *Attorney, Agent, or Firm* — Novel IP

(57) ABSTRACT

Methods for diagnosing if a patient is suffering from a stroke include: positioning a headset around the patient's head to receive vibrations generated by a cerebral vasculature of the patient's brain, the headset including at least one microphone or accelerometer; processing the received vibrations to obtain a signal; analyzing the signal to identify a pattern indicative of a stroke; and determining that the patient is suffering from a stroke based upon the result of a CT scan of the patient's brain and neck and the identified pattern indicative of a stroke.

20 Claims, 22 Drawing Sheets

Related U.S. Application Data

(60) Provisional application No. 63/008,285, filed on Apr. 10, 2020, provisional application No. 62/767,038, filed on Nov. 14, 2018, provisional application No. 62/655,752, filed on Apr. 10, 2018.

(58) Field of Classification Search
CPC ..... A61B 5/4088; A61B 5/4094; A61B 5/165; A61B 5/7405; A61B 5/7445; A61B 5/0022; A61B 5/7264; A61B 5/4824; A61B 5/7282; A61B 7/04; A61B 2562/06; A61B 2562/0204; A61B 2562/0219; A61B 8/481; A61B 2562/04; A61B 2562/046; A61B 5/0024; A61B 5/02028; A61B 5/02438; A61B 5/029; A61B 5/282; A61B 5/316; A61B 5/346; A61B 5/352; A61B 5/6823; A61B 5/6831; A61B 5/7203; A61B 5/725; A61B 5/7257; A61B 5/7267; A61B 7/02; A61B 7/026; A61B 8/0891; A61B 8/4477; A61B 8/5223; A61B 8/56; A61B 5/0077; A61B 5/01; A61B 5/02055; A61B 5/021; A61B 5/112; A61B 5/4076; A61B 5/681; A61B 5/6834; A61B 5/6898; A61B 5/742; A61B 5/743; A61B 6/501; A61B 6/5247; A61B 8/06; A61B 8/4281; A61B 8/4416; G16H 50/20; G16H 40/67; G16H 50/30; A61N 7/00; A61F 2007/0007; A61F 2007/0008; A61F 2007/0009; A61F 2007/0075; A61F 2007/0086; A61F 2007/0093; A61F 2007/0094; A61F 2007/0096; A61F 7/007; A61H 23/0236; A61H 23/0245; G01D 11/18; G01L 1/146; G01L 1/2231; G01L 25/00

USPC .................................................. 600/595, 586

See application file for complete search history.

(56) References Cited

U.S. PATENT DOCUMENTS

| | | |
|---|---|---|
| 5,919,144 A | 7/1999 | Bridger |
| 6,491,647 B1 | 12/2002 | Bridger |
| 6,887,199 B2 | 5/2005 | Bridger |
| 7,720,530 B2 | 5/2010 | Causevic |
| 7,865,244 B2 | 1/2011 | Giftakis |
| 7,904,144 B2 | 3/2011 | Causevic |
| 7,945,316 B2 | 5/2011 | Giftakis |
| 8,041,418 B2 | 10/2011 | Giftakis |
| 8,041,419 B2 | 10/2011 | Giftakis |
| 8,068,911 B2 | 11/2011 | Giftakis |
| 8,108,038 B2 | 1/2012 | Giftakis |
| 8,108,046 B2 | 1/2012 | Giftakis |
| 8,112,148 B2 | 2/2012 | Giftakis |
| 8,112,153 B2 | 2/2012 | Giftakis |
| 8,209,009 B2 | 6/2012 | Giftakis |
| 8,209,019 B2 | 6/2012 | Giftakis |
| 8,214,035 B2 | 7/2012 | Giftakis |
| 8,239,030 B1 | 8/2012 | Hagedorn |
| 8,380,316 B2 | 2/2013 | Hagedorn |
| 8,473,024 B2 | 6/2013 | Causevic |
| 8,478,394 B2 | 7/2013 | Prichep |
| 8,485,979 B2 | 7/2013 | Giftakis |
| 8,744,562 B2 | 6/2014 | Giftakis |
| 8,761,868 B2 | 6/2014 | Giftakis |
| 8,792,974 B2 | 7/2014 | Rothman |
| 8,838,227 B2 | 9/2014 | Causevic |
| 8,838,247 B2 | 9/2014 | Hagedorn |
| 8,905,932 B2 | 12/2014 | Lovoi |
| 8,911,087 B2 | 12/2014 | Publicover |
| 8,938,301 B2 | 1/2015 | Hagedorn |
| 8,942,813 B1 | 1/2015 | Hagedorn |
| 8,948,860 B2 | 2/2015 | Causevic |
| 8,958,882 B1 | 2/2015 | Hagedorn |
| 8,989,836 B2 | 3/2015 | Machon |
| 9,165,472 B2 | 10/2015 | Hagedorn |
| D743,039 S | 11/2015 | Hagedorn |
| 9,198,587 B2 | 12/2015 | Rothman |
| 9,269,046 B2 | 2/2016 | Rothman |
| 9,282,930 B2 | 3/2016 | Machon |
| 9,477,813 B2 | 10/2016 | Rothman |
| RE46,189 E | 11/2016 | Prichep |
| D771,823 S | 11/2016 | Hagedorn |
| 9,629,568 B2 | 4/2017 | Hagedorn |
| 9,711,056 B1 | 7/2017 | Nguyen |
| D799,050 S | 10/2017 | Hagedorn |
| 9,788,747 B2 | 10/2017 | Hagedorn |
| 9,877,664 B2 | 1/2018 | Machon |
| 9,931,069 B2 | 4/2018 | Publicover |
| 10,092,195 B2 | 10/2018 | Lovoi |
| 10,548,501 B2 | 2/2020 | Hagedorn |
| 10,660,537 B2 | 5/2020 | Hagedorn |
| 10,780,268 B2 | 9/2020 | Hagedorn |
| 11,076,797 B2 | 8/2021 | Bobo |
| 2004/0049105 A1 | 3/2004 | Crutchfield |
| 2005/0038342 A1 | 2/2005 | Mozayeni |
| 2005/0124897 A1 | 6/2005 | Chopra |
| 2006/0135877 A1 | 6/2006 | Giftakis |
| 2006/0135881 A1 | 6/2006 | Giftakis |
| 2006/0136006 A1 | 6/2006 | Giftakis |
| 2006/0195144 A1 | 8/2006 | Giftakis |
| 2006/0224067 A1 | 10/2006 | Giftakis |
| 2007/0032737 A1 | 2/2007 | Causevic |
| 2007/0150025 A1 | 6/2007 | Dilorenzo |
| 2007/0238939 A1 | 10/2007 | Giftakis |
| 2007/0239054 A1 | 10/2007 | Giftakis |
| 2007/0239060 A1 | 10/2007 | Giftakis |
| 2007/0239230 A1 | 10/2007 | Giftakis |
| 2007/0260147 A1 | 11/2007 | Giftakis |
| 2007/0260286 A1 | 11/2007 | Giftakis |
| 2007/0260289 A1 | 11/2007 | Giftakis |
| 2007/0265536 A1 | 11/2007 | Giftakis |
| 2007/0265677 A1 | 11/2007 | Giftakis |
| 2008/0033490 A1 | 2/2008 | Giftakis |
| 2008/0208073 A1 | 8/2008 | Causevic |
| 2009/0247894 A1 | 10/2009 | Causevic |
| 2009/0264785 A1 | 10/2009 | Causevic |
| 2010/0041962 A1 | 2/2010 | Causevic |
| 2010/0049101 A1 | 2/2010 | Chopra |
| 2010/0222694 A1 | 9/2010 | Causevic |
| 2011/0087082 A1 | 4/2011 | Giftakis |
| 2011/0105913 A1 | 5/2011 | Giftakis |
| 2011/0125048 A1 | 5/2011 | Causevic |
| 2011/0144520 A1 | 6/2011 | Causevic |
| 2011/0270117 A1 | 11/2011 | Warwick |
| 2012/0041330 A1 | 2/2012 | Prichep |
| 2012/0083717 A1 | 4/2012 | Alleman |
| 2012/0271377 A1 | 10/2012 | Hagedorn |
| 2012/0293773 A1 | 11/2012 | Publicover |
| 2013/0116015 A1 | 5/2013 | Lee |
| 2013/0184603 A1 | 7/2013 | Rothman |
| 2013/0281759 A1 | 10/2013 | Hagedorn |
| 2014/0051940 A1 | 2/2014 | Messerschmidt |
| 2014/0058292 A1 | 2/2014 | Alford |
| 2014/0257073 A1 | 9/2014 | Machon |
| 2014/0288614 A1 | 9/2014 | Hagedorn |
| 2014/0289172 A1 | 9/2014 | Rothman |
| 2014/0316221 A1 | 10/2014 | Rothman |
| 2014/0350431 A1 | 11/2014 | Hagedorn |
| 2015/0032021 A1 | 1/2015 | Chen |
| 2015/0045606 A1 | 2/2015 | Hagedorn |
| 2015/0051663 A1 | 2/2015 | Hagedorn |
| 2015/0072324 A1 | 3/2015 | Pracar |
| 2015/0112409 A1 | 4/2015 | Hagedorn |
| 2015/0157266 A1 | 6/2015 | Machon |
| 2016/0000354 A1 | 1/2016 | Hagedorn |
| 2016/0015289 A1 | 1/2016 | Simon |
| 2016/0022167 A1 | 1/2016 | Simon |
| 2016/0081608 A1* | 3/2016 | Lovoi ............... A61B 5/024 600/483 |
| 2016/0132654 A1 | 5/2016 | Rothman |

(56) References Cited

U.S. PATENT DOCUMENTS

| | | | |
|---|---|---|---|
| 2016/0151018 | A1 | 6/2016 | Machon |
| 2016/0166190 | A1 | 6/2016 | Publicover |
| 2016/0256130 | A1 | 9/2016 | Hamilton |
| 2016/0278736 | A1 | 9/2016 | Hamilton |
| 2016/0367217 | A1 | 12/2016 | Flores, II |
| 2017/0020454 | A1 | 1/2017 | Keteyian |
| 2017/0027467 | A1 | 2/2017 | Hagedorn |
| 2017/0049611 | A1 | 2/2017 | Rosh Vora |
| 2017/0119347 | A1 | 5/2017 | Flores, II |
| 2017/0127946 | A1 | 5/2017 | Levinson |
| 2017/0188932 | A1 | 7/2017 | Singer |
| 2017/0188992 | A1 | 7/2017 | O'Brien |
| 2017/0188993 | A1 | 7/2017 | Hamilton |
| 2017/0188994 | A1 | 7/2017 | Flores, II |
| 2017/0215760 | A1 | 8/2017 | Hagedorn |
| 2017/0307420 | A1 | 10/2017 | Flores, II |
| 2017/0324437 | A1 | 11/2017 | Ruttler |
| 2018/0020941 | A1 | 1/2018 | Hagedorn |
| 2018/0021021 | A1 | 1/2018 | Zwierstra |
| 2018/0064364 | A1 | 3/2018 | Oziel |
| 2018/0067600 | A1 | 3/2018 | Li |
| 2018/0078165 | A1 | 3/2018 | Machon |
| 2018/0103927 | A1 | 4/2018 | Chung |
| 2018/0103928 | A1 | 4/2018 | Costa |
| 2018/0103992 | A1 | 4/2018 | Guyuron |
| 2019/0021627 | A1 | 1/2019 | Levinson |
| 2019/0307388 | A1 | 10/2019 | Bobo |
| 2021/0369182 | A1 | 12/2021 | Bobo |

FOREIGN PATENT DOCUMENTS

| | | | | | |
|---|---|---|---|---|---|
| AU | 2006275864 | A1 | 2/2007 | | |
| AU | 2009222024 | A1 | 9/2009 | | |
| AU | 2009222024 | B2 | 5/2011 | | |
| AU | 2011292220 | A1 | 3/2013 | | |
| AU | 2013306411 | A1 | 12/2014 | | |
| AU | 2011292220 | B2 | 2/2015 | | |
| AU | 2014226506 | A1 | 10/2015 | | |
| AU | 2013306411 | B2 | 6/2016 | | |
| AU | 2014226506 | B2 | 5/2017 | | |
| AU | 2017202427 | A1 | 5/2017 | | |
| CA | 2616974 | A1 | 2/2007 | | |
| CA | 2939790 | A1 | 2/2007 | | |
| CA | 2717170 | A1 | 9/2009 | | |
| CA | 2784267 | A1 | 7/2011 | | |
| CA | 2808097 | A1 | 2/2012 | | |
| CA | 2836779 | A1 | 11/2012 | | |
| CA | 2873688 | A1 | 7/2013 | | |
| CA | 2904529 | A1 | 9/2014 | | |
| CA | 2616974 | C | 10/2016 | | |
| CA | 2717170 | C | 1/2017 | | |
| CA | 2939790 | C | 1/2017 | | |
| CA | 2992961 | A1 | 1/2017 | | |
| CA | 3008804 | A1 | 7/2017 | | |
| CA | 2904529 | C | 10/2017 | | |
| CN | 102014742 | A | 4/2011 | | |
| CN | 102014742 | B | 9/2013 | | |
| CN | 104519960 | A | 4/2015 | | |
| CN | 105520732 | A | 4/2016 | | |
| DE | 602005026054D1 | | 3/2011 | | |
| EP | 1833557 | A1 | 9/2007 | | |
| EP | 1833558 | A1 | 9/2007 | | |
| EP | 1909643 | A2 | 4/2008 | | |
| EP | 1909643 | A4 | 3/2010 | | |
| EP | 2262422 | A1 | 12/2010 | | |
| EP | 1833557 | B1 | 1/2011 | | |
| EP | 1833558 | B1 | 10/2011 | | |
| EP | 2512332 | A1 | 10/2012 | | |
| EP | 2605700 | A1 | 6/2013 | | |
| EP | 2710515 | A2 | 3/2014 | | |
| EP | 2262422 | B1 | 8/2014 | | |
| EP | 2814387 | A1 | 12/2014 | | |
| EP | 2823760 | A1 | 1/2015 | | |
| EP | 2710515 | A4 | 2/2015 | | |
| EP | 2888004 | A1 | 7/2015 | | |
| EP | 2964083 | A1 | 1/2016 | | |
| EP | 1909643 | B1 | 3/2016 | | |
| EP | 3068294 | A1 | 9/2016 | | |
| EP | 2823760 | B1 | 5/2017 | | |
| EP | 2710515 | B1 | 4/2018 | | |
| EP | 3310261 | A1 | 4/2018 | | |
| EP | 3324841 | A1 | 5/2018 | | |
| HK | 1137634 | A | 8/2010 | | |
| HK | 1156492 | A1 | 5/2014 | | |
| HK | 1200303 | A | 8/2015 | | |
| HK | 1219217 | A | 3/2017 | | |
| HK | 1219640 | A | 4/2017 | | |
| IL | 189163D0 | | 8/2008 | | |
| IL | 207959 | A | 2/2016 | | |
| IL | 207959D0 | | 2/2016 | | |
| IN | 397KOLNP2008 | A | 12/2008 | | |
| IN | 3251KOLNP2010 | A | 11/2010 | | |
| IN | 622KOLN2013 | A | 7/2013 | | |
| IN | 1585MUMNP2014 | A | 5/2015 | | |
| IN | 2928KOLNP2015 | A | 2/2016 | | |
| JP | 2015533526 | A | 11/2015 | | |
| SG | 139858 | A1 | 3/2008 | | |
| WO | WO-2004045426 | A1 * | 6/2004 | ............ | A61B 17/12 |
| WO | WO-2005061053 | A1 * | 7/2005 | ........... | A61B 8/0808 |
| WO | 2006066098 | A1 | 6/2006 | | |
| WO | 2006066099 | A1 | 6/2006 | | |
| WO | 2006066280 | A1 | 6/2006 | | |
| WO | 2006066099 | A9 | 8/2006 | | |
| WO | 2006086075 | A1 | 8/2006 | | |
| WO | 2007016149 | A2 | 2/2007 | | |
| WO | 2007016149 | A3 | 4/2009 | | |
| WO | 2009111426 | A1 | 9/2009 | | |
| WO | 2009129279 | A1 | 10/2009 | | |
| WO | 2009138882 | A2 | 11/2009 | | |
| WO | 2011084394 | A1 | 7/2011 | | |
| WO | 2012024175 | A1 | 2/2012 | | |
| WO | 2012162205 | A2 | 11/2012 | | |
| WO | 2012162205 | A3 | 3/2013 | | |
| WO | 2013063053 | A1 | 5/2013 | | |
| WO | 2013109492 | A1 | 7/2013 | | |
| WO | 2014031142 | A1 | 2/2014 | | |
| WO | 2013109492 | A8 | 8/2014 | | |
| WO | 2014137549 | A1 | 9/2014 | | |
| WO | 2015073903 | A1 | 5/2015 | | |
| WO | 2015187401 | A1 | 12/2015 | | |
| WO | 2016094586 | A1 | 6/2016 | | |
| WO | 2016205824 | A1 | 12/2016 | | |
| WO | 2017013655 | A1 | 1/2017 | | |
| WO | 2017116582 | A1 | 7/2017 | | |
| WO | 2017118964 | A1 | 7/2017 | | |
| WO | 2017120361 | A1 | 7/2017 | | |
| WO | 2017120382 | A1 | 7/2017 | | |
| WO | 2017120388 | A1 | 7/2017 | | |
| WO | 2017189623 | A1 | 11/2017 | | |
| WO | 2018017614 | A1 | 1/2018 | | |
| WO | 2018027298 | A1 | 2/2018 | | |
| WO | 2018075415 | A1 | 4/2018 | | |
| WO | 2018075416 | A1 | 4/2018 | | |
| WO | 2019200001 | A1 | 10/2019 | | |

OTHER PUBLICATIONS

Wikipedia, "Electret microphone", Mar. 28, 2016 (Mar. 28, 2016), retrieved on Jul. 5, 2019 from https://en.wikipedia.org/w/index.php?title=Elecret_microphone&oldid=712378585; entire document, especially p. 1 para 1.

International Search Report for PCT/US19/26833, Sep. 13, 2019.

Voss et al., "Detecting changes in intracranial pressure using ear-canal reflectance and otoacoustic emissions", Hearing Research as part of teh MEMRO group of manuscripts, Jul. 8, 2009.

Poh et al., "Cardiovascular Monitoring Using Earphones and a Mobile Device", IEEE Pervasive Computing, 2010. Digital Object Identifier 10.1109/MPRV.2010.91.

Brennan et al., "An update on the blood vessel in migraine", Curr Opin Neurol. Jun. 2010; 23(3): 266-284. doi: 10.1097/WCO.0b013e32833821c1.

Ganslandt et al., "Evaluation of a novel noninvasive ICP monitoring device in patients undergoing invasive ICP monitoring: preliminary

(56) References Cited

OTHER PUBLICATIONS results" J Neurosurg, Aug. 8, 2017, Published online Aug. 8, 2017; DOI: 10.3171/2016.11.JNS152268.

Canning et al., "Noninvasive and Continuous Blood Pressure Measurement via Superficial Temporal Artery Tonometry", August 2016Conference proceedings: . . . Annual International Conference of the IEEE Engineering in Medicine and Biology Society. IEEE Engineering in Medicine and Biology Society. DOI: 10.1109/EMBC. 2016.7591453.

Mom et al., "Vasospasm of labyrinthine artery in cerebellopontine angle surgery: evidence brought by distortion-product otoacoustic emissions", Eur Arch Otorhinolaryngol (2014) 271:2627-2635, DOI 10.1007/s00405-013-2753-0.

Anonymous: "Electret microphone", Wikipedia, Mar. 28, 2016 (Mar. 28, 2016), XP055643603.

Goverdovsky et al., "Hearables: Multimodal physiological in-ear sensing", Scientific Reports, 7: 6948, DOI:10.1038/s41598-017-06925-2, pp. 1-10, Jul. 31, 2017.

International Search Report for PCT/US21/26539, Jul. 26, 2021.

Written Opinion of the International Searching Authority for PCT/US21/26539, Jul. 26, 2021.

\* cited by examiner

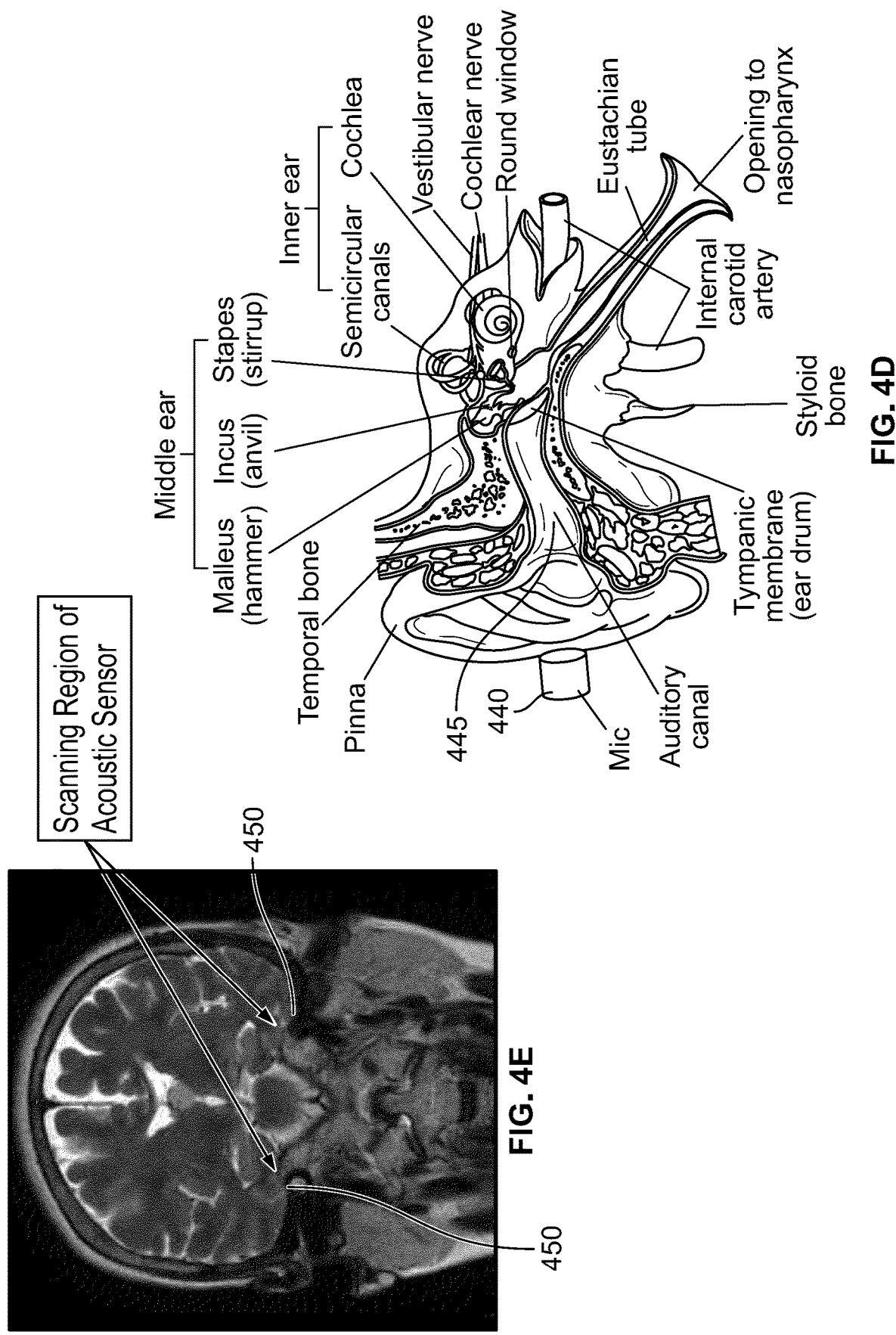

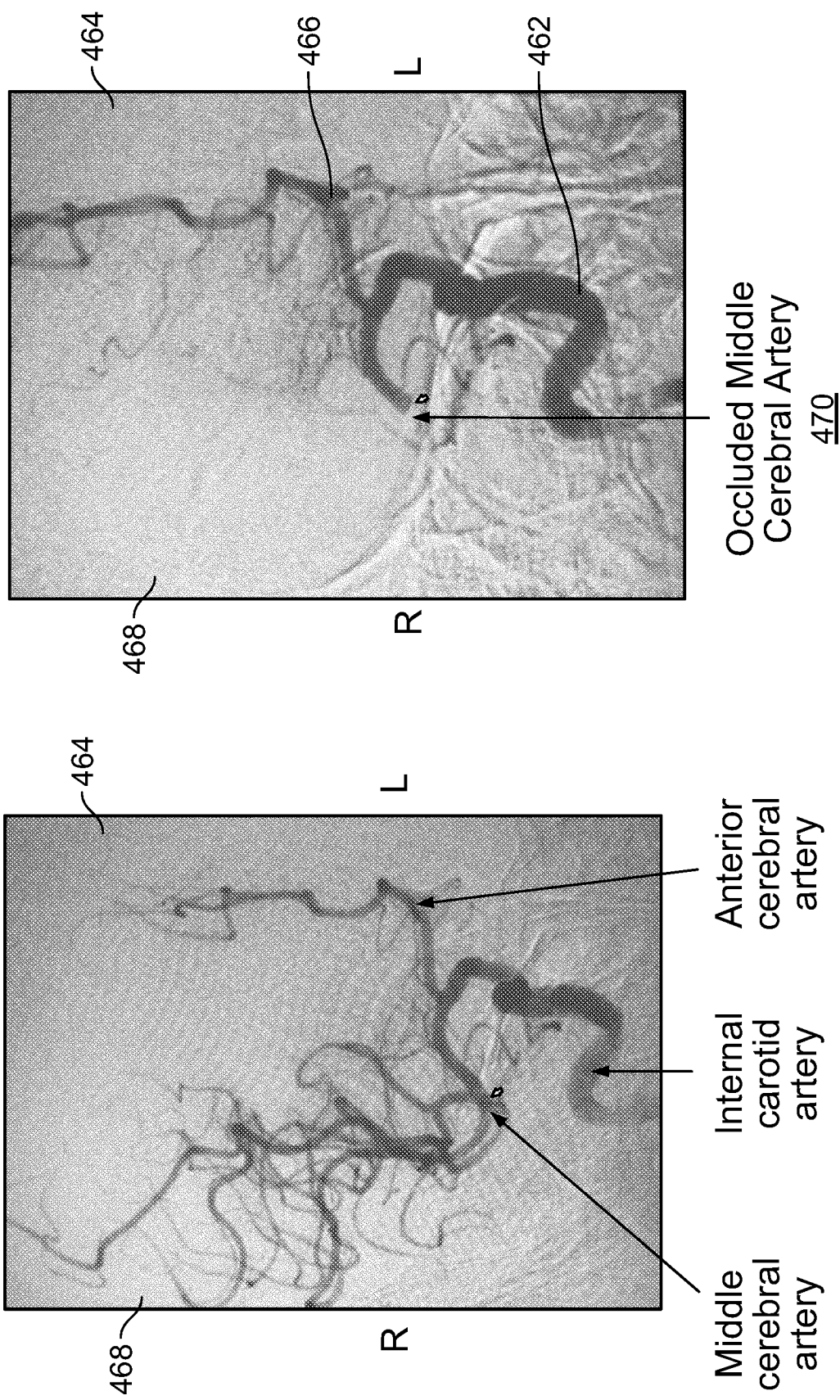

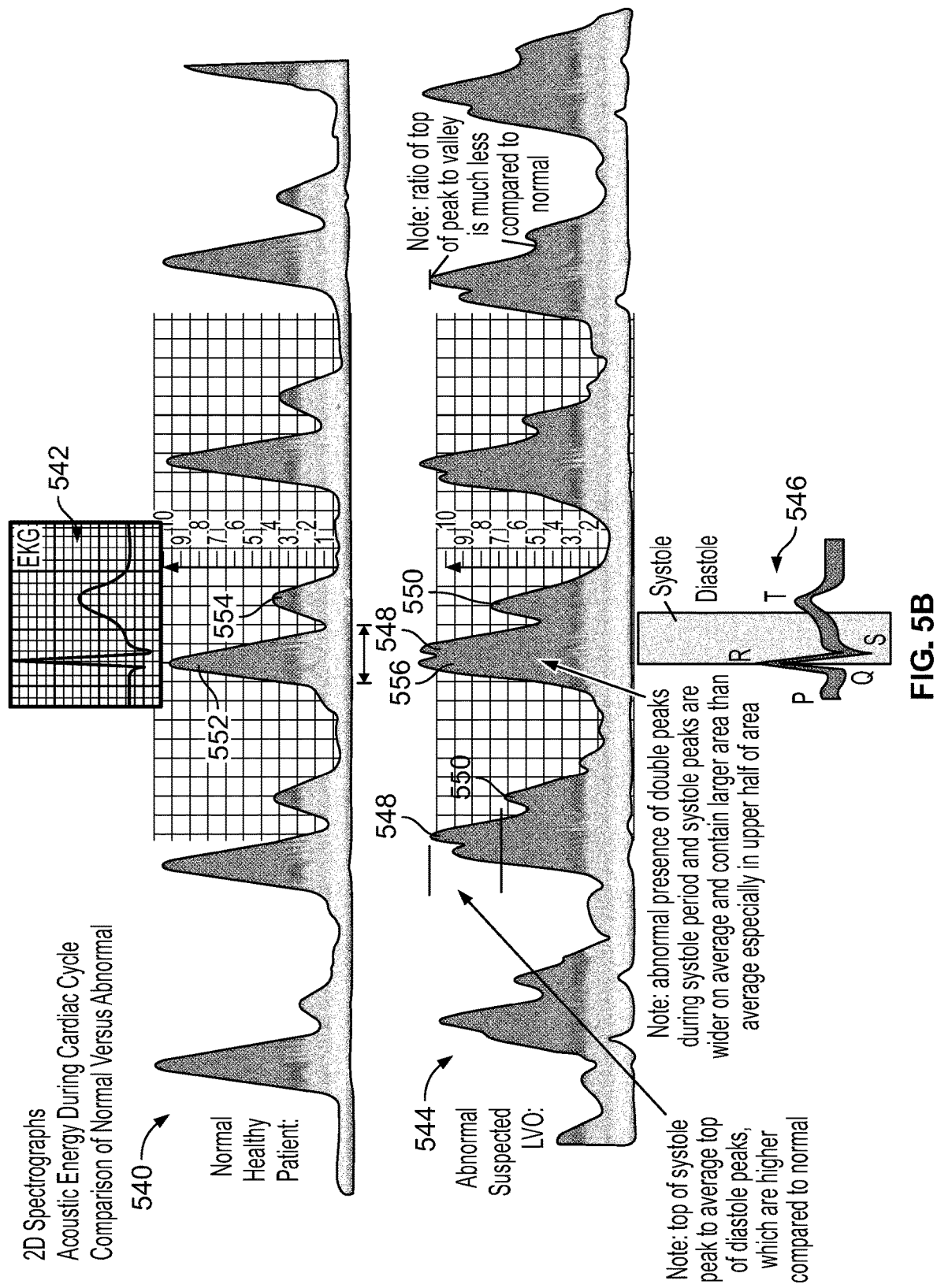

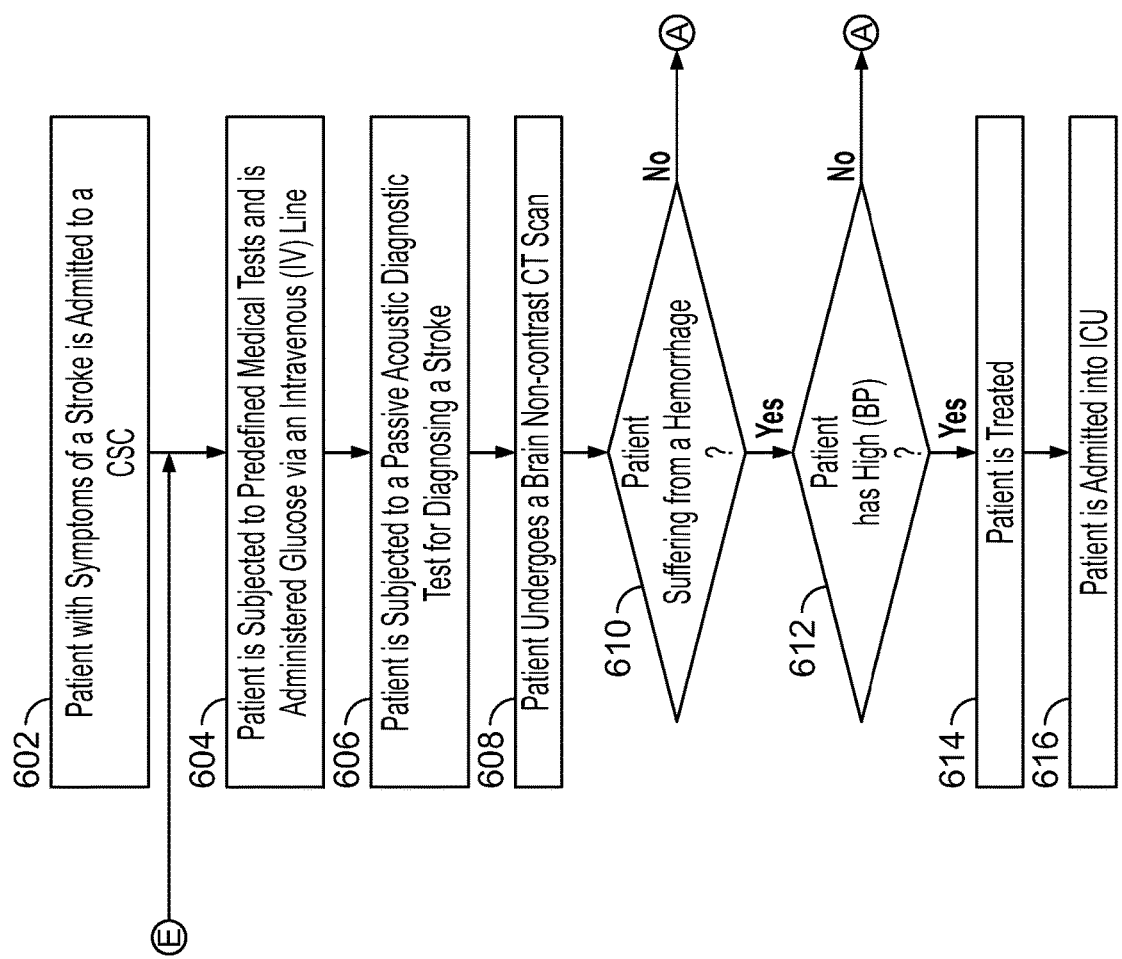

660

Patient Name: Andrew Scott
Patient ID: ANST7345Z

Patient data to be processed to determine hemorrhage

First patient data  
Second patient data  } 662
Third patient data  
Fourth patient data

[Process]

665

Patient Name: Andrew Scott
Patient ID: ANST7345Z

Input Blood Pressure values

Systolic value: [    ] ⎫
                        ⎬ 667
Diastolic value: [    ] ⎭

[Save]

670

Patient Name: Andrew Scott
Patient ID: ANST7345Z

Patient assessment

Audio diagnostic test:  Positive for stroke — 671
CT scan results:        Negative for stroke — 672
No. of hrs. elapsed:    < 4.5 hrs. — 673
(since LKW time)

[Next step] — 674

675

Patient Name: Andrew Scott
Patient ID: ANST7345Z

Recommendation — 677

Administer a Tissue Plasminogen Activator (TPA) to the patient

Patient Name: Andrew Scott
Patient ID: ANST7345Z

680

Recommendation 682

Run at least one of the following tests on the patient

- CT Angiography (CTA) of the brain and neck
- CT Perfusion (CTP)

NON-INVASIVE SYSTEMS AND METHODS FOR THE IMPROVED EVALUATION OF PATIENTS SUFFERING FROM UNDIAGNOSED HEADACHES

CROSS-REFERENCE

The present application relies on U.S. Patent Provisional Application No. 63/008,285, titled "Non-Invasive Systems and Methods for the Improved Evaluation of Patients Suffering From Undiagnosed Headaches", filed on Apr. 10, 2020, for priority, which is herein incorporated by reference in its entirety.

The present specification is also a continuation-in-part application of U.S. patent application Ser. No. 16/380,841 (US Patent Publication No. 2019/0307388), of the same title, filed on Apr. 10, 2019, and issued as U.S. Pat. No. 11,076,797B2 on Aug. 3, 2021, which, in turn, relies on for priority:

U.S. Patent Provisional Application No. 62/767,038, entitled "Systems and Methods for the Diagnosis of Medical Conditions Using a Detection of Signals Generated from Blood Flow in the Brain" and filed on Nov. 14, 2018; and, U.S. Patent Provisional Application No. 62/655,752, entitled "Neurological Diagnostic and Therapeutic Device and Method" and filed on Apr. 10, 2018.

All of the above-mentioned applications are herein incorporated by reference in their entirety.

FIELD

The present specification relates generally to systems and method for evaluating a patient suffering from an undiagnosed headache, including pain that may be associated with a stroke arising from a large vessel occlusion or a migraine. More specifically, the present specification relates to systems and methods for a field diagnosis that differentiates between at least strokes or migraines by passively detecting signals generated from blood flowing through the cerebral blood vessels of the patient using microphones or accelerometers and analyzing them for certain signatures.

BACKGROUND

A stroke is a sudden interruption in the blood flowing through the cerebral blood vessels. Most strokes are caused by an abrupt blockage of arteries leading to the brain and are known as ischemic strokes, while others are caused by occurrence of a bleeding into brain tissue when a blood vessel bursts and are called hemorrhagic strokes. Strokes may occur because of a large vessel occlusion (LVO) i.e. a blockage in a blood vessel carrying blood to parts of the brain. Most LVOs may be an occlusion of either the internal carotid artery (ICA), anterior cerebral artery (ACA) or middle cerebral artery (MCA).

Currently, a patient presenting with symptoms of LVO in an Emergency Room (ER) is subjected to an emergent head CT in order to determine if the patient has sustained an intracerebral injury. The patient subsequently undergoes neurosurgical or neurologic care to minimize brain damage and preserve life. If the CT of the brain discloses no evidence of stroke, but the patient continues to be symptomatic, thrombolytic therapy via IV infusion is instituted. This medication is Tissue Plasminogen Activator (TPA), and the patient is subsequently subjected to a CT arteriogram (CTA) and/or a CT perfusion (CTP) to determine the presence of an LVO. If an LVO is identified on the CTA/CTP, the patient undergoes predefined medical procedures such as, but not limited to a catheter angiogram and mechanical thrombectomy. In cases where the emergent head CT is non-conclusive, the patient is still injected with the TPA and tested by using CTA and CTP procedures. This is both time consuming and resource intensive and may, in some cases, only aid in ruling out a stroke but not diagnosing the underlying condition.

Samuel Jones Gee (1839-1911) stated that "[w]hatever constricts an orifice, whatever dilates a cavity, whatever establishes an orifice or cavity where none shall be, will disturb the even flow of blood and produce vibrations and a murmur". The following references are herein incorporated by reference in their entirety:

Allen N, Mustian V. Origin and significance of vascular murmurs of the head and neck. *Medicine* (Baltimore). 1962; 41:227-47

Barnes R W. Hemodynamics for the vascular surgeon. *Arch. Surg.* 1980; 115:216-23.

Barnett H J M, Plum F, Walton J N. Carotid endarterectomy—an expression of concern. *Stroke.* 1984; 15:941-943, explains that a Bruit, also called vascular murmur, is the abnormal sound generated by turbulent flow of blood in an artery due to either an area of partial obstruction or a localized high rate of blood flow through an unobstructed artery.

Beasley M G, Blau J N, Gosling R G. Changes in internal carotid artery flow velocities with cerebral vasodilation and constriction. *Stroke.* 1979; 10:331-35 explains that cranial auscultation, is listening to the sounds in the head created by the cardiac cycle and complex of reactions through the vasculature. Turbulent blood flow may also be audible due to other reasons, some of them pathological. For example, in advanced atherosclerosis, bruits (and therefore turbulent flow) can be heard in some vessels that have been narrowed by the disease process. Indication for cranial auscultation usually follows from historical physical examination or laboratory evidence of cranial-cervical disorders such as seizures, headaches, stroke syndromes, intracranial mass lesions, or carotid bruits.

As provided in 'Diagnostic: evaluation of the carotid arteries. Health and Public Policy Committee, American College of Physicians. *Ann. Intern. Med.* 1988; 109:835-37, cranial auscultation should be carried out over or near the temporal fossa and mastoid processes, both of which are close enough to the ear canal that such sounds can readily be detected with a sensitive listening apparatus (sensors) over the head including coverage over the ears.

Additional sensor(s) may be placed over the neck to more accurately determine location of a bruit in the carotid artery or cervical veins (cervical venous hum), or arteriovenous (AV) connections (intracranial AV malformations) with other factors altering intensity and duration of arterial bruits (A-V=arteriovenous; CHF=congestive heart failure) as provided in Edwards F. A, Levin HD. Peripheral vascular murmurs: Mechanism of production and diagnostic significance. *Arch. Intern. Med.* 1952; 90:284-300, as indicated in the figures and, in particular, the figure entitled "Arterial Bruits—Dynamic Alteration"].

Fowler N O, Marshall W J. The supraclavicular arterial bruit. *Am. Heart J.* 1965; 69:410-18

Hurst J W, Hopkins L C, Smith R B III. Noises in the neck. *N. Engl. J. Med.* 1980; 302:862-63

Kurtz K J. Dynamic vascular auscultation. *Am. J. Med.* 1984; 76:1066-74

Lees R S. The natural history of carotid artery disease. *Stroke.* 1984; 15:603-4

MacKenzie I. The intracranial bruit. *Brain.* 1955; 78:350-68

Reed C A, Toole J F. Clinical technique for identification of external carotid bruits. *Neurology.* 1981; 31:744-46; and Toole J F. Surgery for patients with carotid-artery murmurs. *N. Engl. J. Med.* 1982; 307:1401

Currently, there are no available reliable diagnostic devices to provide quick, efficient and non-invasive ways of distinguishing between strokes, migraines, seizures, and other brain-related conditions that are not obviously caused by a traumatic injury and to deliver an objective and quantitative assessment of the patient's condition. Patients usually have to undergo elaborate examination procedures such as taking injections of a contrast creating material (such as TPA) and then undergoing specialized computer tomography (CT) scans, which are time consuming, tedious and expensive.

Therefore, there is a need for an objective means to determine the nature of a patient's condition and thereby help diagnose a spectrum of brain-related non-traumatic disease conditions such as a stroke, and guide medical to providing the optimum therapies. There is also a need for a diagnostic system and method that would enable quick efficient and cost-effective diagnosis of strokes. There is also a need for a diagnostic system and method that would provide the requisite data needed to distinguish between strokes, migraines, brain hemorrhages, seizures, and other brain-related non-traumatic disease conditions. There is also a need for a non-invasive system that can monitor a patient's recovery from symptoms of brain-related non-traumatic disease conditions for which the patient is receiving treatment.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a diagnostic system for triaging a patient suffering from a brain condition, the system comprising: a head worn device comprising at least one acoustic sensor configured to passively detect vibrations generated by a cerebral vasculature of the patient's brain; a software program configured to execute on a mobile computing device, wherein, when executed, the software program is configured to: present a plurality of graphical user interfaces configured to direct a user through a triaging process for the patient; receive data indicative of the passively detected vibrations; and process the data to obtain at least one signal; and a signal analyzer coupled with the software program and configured to analyze the signal to identify a pattern indicative of a large vessel occlusion.

Optionally, the signal analyzer is optimized to identify a large vessel occlusion relative to any other brain condition.

Optionally, the pattern indicative of a large vessel occlusion is defined, at least in part, by a difference between a maximum height of a systole peak in the signal to a maximum height of a diastole peak adjacent to the systole peak in the signal being less than a difference between a maximum height of a systole peak and a maximum height of an adjacent diastole peak in a reference signal.

Optionally, the pattern indicative of a large vessel occlusion is defined, at least in part, by a greater number of double systole peaks in the signal relative to a reference signal, wherein a double systole peak is defined as a temporal sequence of a first systole peak, a first valley, a second systole peak, a second valley, and a diastole peak and wherein the reference signal is a signal derived from passively received vibrations of a person who does not have a large vessel occlusion.

Optionally, the pattern indicative of a large vessel occlusion is defined, at least in part, by a ratio of a maximum height of a systole peak in the signal relative to a minimum height of a valley adjacent to the systole peak being less than a ratio of a maximum height of a systole peak in a reference signal relative to a minimum height of a valley adjacent to the systole peak in the reference signal and wherein the reference signal is a signal derived from passively received vibrations of a person who does not have a large vessel occlusion.

Optionally, at least one of the plurality of graphical user interfaces prompts the user for data indicative of a CT scan of the patient's brain.

Optionally, at least one of the plurality of graphical user interfaces prompts the user for data indicative of a stroke scale exam.

Optionally, at least one of the plurality of graphical user interfaces prompts the user for data indicative of whether the patient suffers from a hemorrhage.

Optionally, at least one of the plurality of graphical user interfaces prompts the user for data indicative of at least one of the patient's heart rate or blood pressure.

Optionally, if a large vessel occlusion is not identified, the signal analyzer is further configured to analyze the signal to identify a pattern indicative of a migraine.

Optionally, if a large vessel occlusion is not identified, the software program is further configured to activate the head worn device to passively detect a second set of vibrations generated by the cerebral vasculature of the patient's brain, receive data indicative of the second set of detected vibrations from the head worn device, and process the data indicative of the second set of detected vibrations to obtain a second signal. Optionally, the signal analyzer is further configured to analyze the second signal to identify a pattern indicative of a migraine.

Optionally, the software program is further configured to process at least one of imaging data or physical exam data together with the identified pattern to generate a determination of whether the patient is undergoing a stroke and to display the determination in at least one of the plurality of graphical user interfaces.

Optionally, the software program is further configured to display, in at least one of the plurality of graphical user interfaces, a first recommendation if at least one of imaging data or physical exam data indicates the patient is having a stroke and if the identified pattern does not indicate the patient is having a stroke. Optionally, the software program is further configured to display, in at least one of the plurality of graphical user interfaces, a second recommendation if at least one of imaging data or physical exam data indicates the patient is having a stroke and if the identified pattern also indicates the patient is having a stroke, wherein the first recommendation is different from the second recommendation.

The present specification also discloses a system for diagnosing a patient suffering from a brain condition, the system comprising: a head worn device comprising at least one acoustic sensor configured to passively detect vibrations generated by a cerebral vasculature of the patient's brain; a software program configured to execute on a mobile computing device, wherein, when executed, the software program is configured to: receive at least one of blood work data, historical treatment data, physical exam data, or imaging data of the patient; receive data indicative of the passively detected vibrations; and process the data to obtain at least one signal; and a signal analyzer coupled with the software program and configured to analyze the signal to identify a pattern indicative of at least one of a large vessel occlusion, stroke, or migraine, wherein the software program is configured to process the at least one of blood work data, physical exam data, historical treatment data or imaging data together with the identified pattern to generate a diagnosis of the patient and is configured to display the generated diagnosis in at least one graphical user interface, and wherein the diagnosis indicates whether the patient is suffering from at least one of a large vessel occlusion, stroke or migraine.

Optionally, the pattern indicative of a large vessel occlusion is defined, at least in part, by a difference between a maximum height of a systole peak in the signal to a maximum height of a diastole peak adjacent to the systole peak in the signal being less than a difference between a maximum height of a systole peak and a maximum height of an adjacent diastole peak in a reference signal.

Optionally, the pattern indicative of a large vessel occlusion is defined, at least in part, by a greater number of double systole peaks in the signal relative to a reference signal, wherein a double systole peak is defined as a temporal sequence of a first systole peak, a first valley, a second systole peak, a second valley, and a diastole peak and wherein the reference signal is a signal derived from passively received vibrations of a person who does not have a large vessel occlusion.

Optionally, the pattern indicative of a large vessel occlusion is defined, at least in part, by a ratio of a maximum height of a systole peak in the signal relative to a minimum height of a valley adjacent to the systole peak being less than a ratio of a maximum height of a systole peak in a reference signal relative to a minimum height of a valley adjacent to the systole peak in the reference signal and wherein the reference signal is a signal derived from passively received vibrations of a person who does not have a large vessel occlusion.

Optionally, the signal analyzer is optimized to first identify a large vessel occlusion relative to a migraine.

The present specification also discloses a diagnostic system for triaging a patient suffering from a brain condition, the system comprising: a headset comprising at least one acoustic sensor and configured to passively receive vibrations generated by a cerebral vasculature of the patient's brain; a software program configured to execute on a mobile computing device, wherein, when executed, the software program is configured to: present a plurality of graphical user interfaces configured to direct a user through a triaging process receive data indicative of the passively received vibrations; process the data to obtain at least one signal; and a signal analyzer coupled with the software program and configured to analyze the signal to identify a pattern indicative of a stroke, wherein the diagnosis is based upon the result of a non-contrast CT scan of the patient's brain and neck and the identified pattern indicative of a stroke.

Optionally, if the pattern is indicative of a stroke and the result is not indicating a stroke, the patient is subjected to a contrast CTA and CTP for determining if the patient is suffering from one of an LVO, or an AF.

Optionally, if the pattern is indicative of a stroke and the result is indicating a stroke, the patient is subjected to a contrast CTA and CTP for determining if the patient is suffering from one of an LVO, or an AF.

Optionally, if the pattern is not indicative of a stroke and the result is indicating a stroke determining that the patient is suffering from a chronic stroke condition.

Optionally, if the pattern is not indicative of a stroke and the result is not indicating a stroke determining that the patient is not suffering from a stroke.

Optionally, the signal analyzer identifies a pattern indicative of a stroke by executing one or more algorithms configured to detect a stroke by comparing the analyzed signal with one or more pre-determined signal classifications comprising specific frequencies unique to a stroke. Optionally, the pre-determined signal classifications comprises specific frequencies, frequency ranges, energies, energy ranges, periodicities or periodicity ranges unique to strokes.

Optionally, the signal analyzer identifies a pattern indicative of a stroke by identifying vibrations of specific pre-defined frequencies generated by the cerebral vasculature of the patient's brain due to blocked blood vessels.

Optionally, the at least one microphone captures and outputs bi-hemispheric data and has an output for detecting vibration in a range of 0-750 kHz.

The present specification also discloses a method for determining if a patient is suffering from a stroke, the method comprising: positioning a headset around the patient's head to passively receive vibrations generated by a cerebral vasculature of the patient's brain, the headset comprising at least one microphone or accelerometer; processing the received vibrations to obtain a signal; analyzing the signal to identify a pattern indicative of a stroke; conducting a CT scan of the patient's brain and neck to obtain a result indicating if the patient is suffering from a stroke; if the pattern is indicative of a stroke and the result is not indicating a stroke, subjecting the patient to a contrast CTA and CTP for determining if the patient is suffering from one of an LVO or an AF; if the pattern is indicative of a stroke and the result is indicating a stroke, subjecting the patient to a contrast CTA and CTP for determining if the patient is suffering from one of an LVO or an AF; if the pattern is not indicative of a stroke and the result is indicating a stroke determining that the patient is suffering from a chronic stroke condition; and if the pattern is not indicative of a stroke and the result is not indicating a stroke determining that the patient is not suffering from a stroke.

Optionally, the method further comprises using the identified pattern and the result to determine if the patient is suffering from a brain hemorrhage. Optionally, the method further comprises determining that the patient's blood pressure is below a threshold value for determining one or more predefined medical procedures for treating the patient's brain hemorrhage.

Optionally, the method further comprises using the identified pattern to determine if the patient is suffering from migraine, if the patient is determined as not suffering from a stroke.

Optionally, the method further comprises determining if the patient is suffering from seizures if the pattern is not indicative of a stroke and the result is not indicating a stroke.

Optionally, analyzing the signal to identify a pattern indicative of a stroke comprises executing one or more algorithms configured to detect a stroke by comparing the analyzed signal with one or more pre-determined signal classifications comprising specific frequencies unique to a stroke. Optionally, the pre-determined signal classifications comprise specific frequencies, frequency ranges, energies, energy ranges, periodicities or periodicity ranges unique to strokes.

Optionally, analyzing the signal to identify a pattern indicative of a stroke comprises identifying vibrations of specific predefined frequencies generated by the cerebral vasculature of the patient's brain due to blocked blood vessels. Optionally, the vibrations of specific predefined frequencies being generated due to walls of an occluded artery leads being rigidly expanded and loosened with each heartbeat of the patient.

Optionally, the method further comprises receiving vibrations generated by a cerebral vasculature of the patient's brain periodically over predefined intervals of time after the commencement of a treatment for stroke, if it is determined that the patient is suffering from a stroke.

The present specification also discloses a method for diagnosing if a patient is suffering from a stroke, the method comprising: positioning a headset around the patient's head to passively receive vibrations generated by a cerebral vasculature of the patient's brain, the headset comprising at least one microphone or accelerometer; processing the received vibrations to obtain a signal; analyzing the signal to identify a pattern indicative of a stroke; and determining that the patient is suffering from a stroke based upon the result of a CT scan of the patient's brain and neck and the identified pattern indicative of a stroke.

In some embodiments, the present specification is directed towards a method for determining if a patient is suffering from a stroke, the method comprising: positioning a headset around the patient's head to passively receive vibrations generated by a cerebral vasculature of the patient's brain, the headset comprising at least one microphone or accelerometer; processing the received vibrations to obtain a signal; analyzing the signal to identify a pattern indicative of a stroke; conducting a CT scan of the patient's brain and neck to obtain a result indicating if the patient is suffering from a stroke; if the pattern is indicative of a stroke and the result is not indicating a stroke, subjecting the patient to a contrast CTA and CTP for determining if the patient is suffering from one of an LVO or an AF; if the pattern is indicative of a stroke and the result is indicating a stroke, subjecting the patient to a contrast CTA and CTP for determining if the patient is suffering from one of an LVO or an AF; if the pattern is not indicative of a stroke and the result is indicating a stroke determining that the patient is suffering from a chronic stroke condition; and if the pattern is not indicative of a stroke and the result is not indicating a stroke determining that the patient is not suffering from a stroke.

Optionally, the method further comprises using the identified pattern and the result to determine if the patient is suffering from a brain hemorrhage.

Optionally, the method further comprises determining that the patient's blood pressure is below a threshold value for determining one or more predefined medical procedures for treating the patient's brain hemorrhage.

Optionally, the method further comprises using the identified pattern to determine if the patient is suffering from migraine, if the patient is determined as not suffering from a stroke.

Optionally, the method further comprises determining if the patient is suffering from seizures if the pattern is not indicative of a stroke and the result is not indicating a stroke.

Optionally, analyzing the signal to identify a pattern indicative of a stroke comprises executing one or more algorithms configured to detect a stroke by comparing the analyzed signal with one or more pre-determined signal classifications comprising specific frequencies unique to a stroke.

Optionally, the pre-determined signal classifications comprise specific frequencies, frequency ranges, energies, energy ranges, periodicities or periodicity ranges unique to strokes.

Optionally, analyzing the signal to identify a pattern indicative of a stroke comprises identifying vibrations of specific predefined frequencies generated by the cerebral vasculature of the patient's brain due to blocked blood vessels. Optionally, the vibrations of specific predefined frequencies being generated due to walls of an occluded artery leads being rigidly expanded and loosened with each heartbeat of the patient.

Optionally, the method further comprises receiving vibrations generated by a cerebral vasculature of the patient's brain periodically over predefined intervals of time after the commencement of a treatment for stroke, if it is determined that the patient is suffering from a stroke.

In some embodiments, the present specification discloses a system for diagnosing if a patient is suffering from a stroke, the system comprising: a headset comprising at least one microphone or accelerometer to passively receive vibrations generated by a cerebral vasculature of the patient's brain; at least one computing device coupled with the headset for processing the received vibrations to obtain a signal; and a signal analyzer coupled with the at least one computing device and configured to analyze the signal to identify a pattern indicative of a stroke, wherein the diagnosis is based upon the result of a non-contrast CT scan of the patient's brain and neck and the identified pattern indicative of a stroke.

Optionally, if the pattern is indicative of a stroke and the result is not indicating a stroke, the patient is subjected to a contrast CTA and CTP for determining if the patient is suffering from one of an LVO, or an AF.

Optionally, if the pattern is indicative of a stroke and the result is indicating a stroke, the patient is subjected to a contrast CTA and CTP for determining if the patient is suffering from one of an LVO, or an AF.

Optionally, if the pattern is not indicative of a stroke and the result is indicating a stroke determining that the patient is suffering from a chronic stroke condition.

Optionally, if the pattern is not indicative of a stroke and the result is not indicating a stroke determining that the patient is not suffering from a stroke.

Optionally, the signal analyzer identifies a pattern indicative of a stroke by executing one or more algorithms configured to detect a stroke by comparing the analyzed signal with one or more pre-determined signal classifications comprising specific frequencies unique to a stroke.

Optionally, the pre-determined signal classifications comprises specific frequencies, frequency ranges, energies, energy ranges, periodicities or periodicity ranges unique to strokes.

Optionally, the signal analyzer identifies a pattern indicative of a stroke by identifying vibrations of specific predefined frequencies generated by the cerebral vasculature of the patient's brain due to blocked blood vessels.

Optionally, the at least one microphone captures and outputs bi-hemispheric data and has an output for detecting vibration in a range of 0-750 kHz.

In some embodiments, the present specification discloses a method for diagnosing if a patient is suffering from a stroke, the method comprising: positioning a headset around the patient's head to passively receive vibrations generated by a cerebral vasculature of the patient's brain, the headset comprising at least one microphone or accelerometer; processing the received vibrations to obtain a signal; analyzing the signal to identify a pattern indicative of a stroke; and determining that the patient is suffering from a stroke based upon the result of a CT scan of the patient's brain and neck and the identified pattern indicative of a stroke.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the detailed description when considered in connection with the accompanying drawings:

FIG. 4D illustrates microphones placed near the ear canal of a person, in accordance with an embodiment of the present specification;

FIG. 4E illustrates scanning regions of acoustic sensors within the brain of a person, in accordance with an embodiment of the present specification;

FIG. 4F illustrates blood flow from an internal carotid artery to left and right parts of a person's brain.

FIG. 4G illustrates an occluded middle cerebral artery restricting the flow of blood to the right part of the person's brain shown in FIG. 4F;

FIG. 5B illustrates a spectrogram of a healthy person compared with a spectrogram of a patient suffering from a stroke, in accordance with an embodiment of the present specification;

FIG. 6B illustrates a plurality of exemplary GUIs (Graphical User Interfaces) generated by the assessment application in the context of the method of FIG. 6A, in accordance with some embodiments of the present specification.

DETAILED DESCRIPTION

Since a bruit may be heard ("auscultated") by securely placing a sensitive listening device near the suspected area of turbulent flow, and converting the sounds to digital data (digitizing the waveform), the present specification provides a method of analysis of said data using a computer algorithm which is capable of: determining various energies at various frequencies at specific phases of the cardiac periodicity, determining spectral changes ("spectral shifts") relative to normal. Most bruits occur only in systole cardiac phase (each initial outflow pulsation phase of the heart), so the bruit is intermittent and its frequency dependent on the heart rate. However, these bruits may extend into diastole or even be continuous. Anything increasing the blood flow velocity such as fever, anemia, hyperthyroidism, low blood oxygen, or physical exertion, can increase the amplitude of the bruit and anything which blocks normal blood flow, such as an LVO, may be auscultated and sent to a computer for analysis of the spectral data in three dimensions of time, energy and frequency.

Figure 1A:
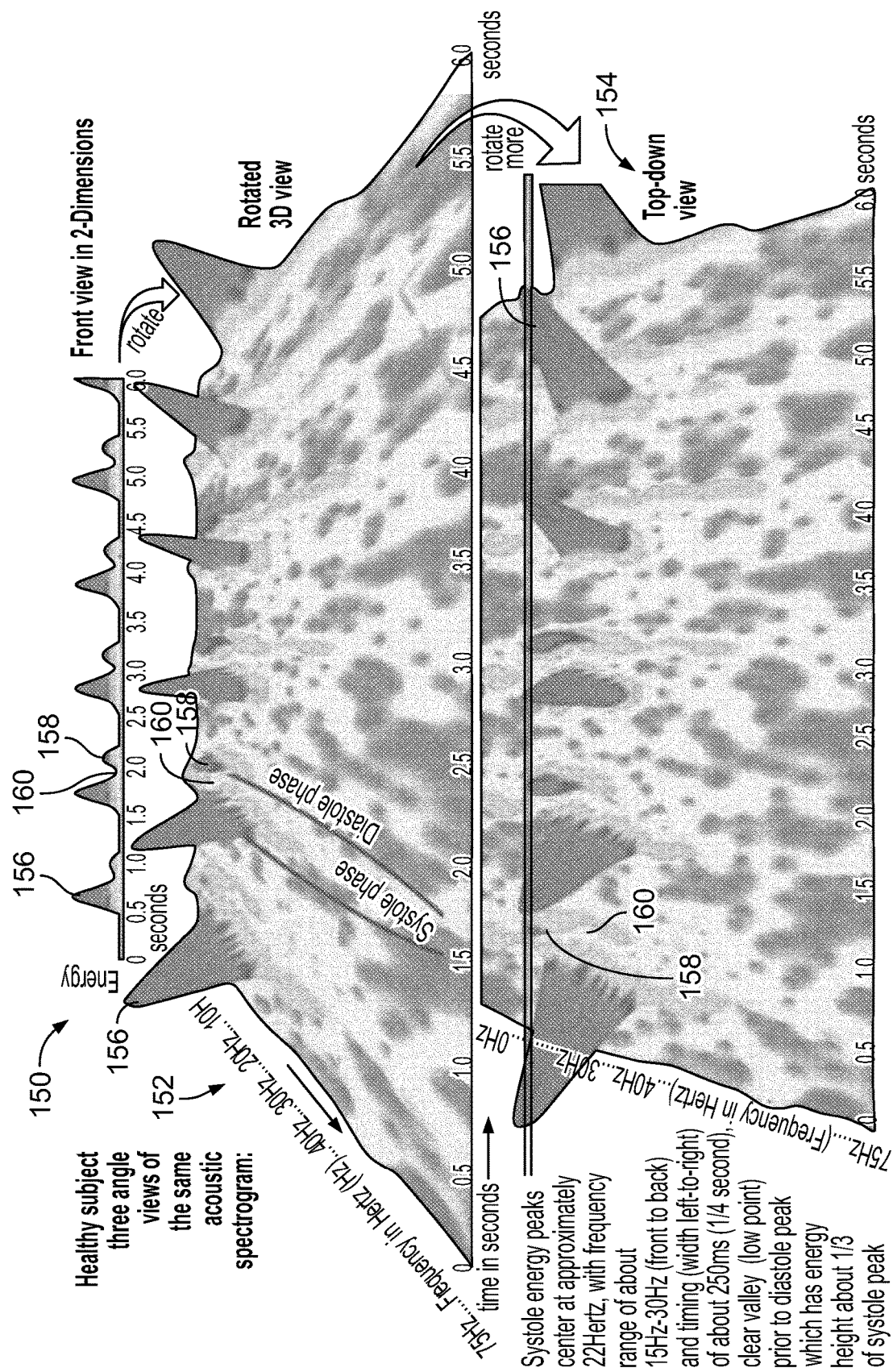
FIG. 1A illustrates three angle views of a healthy person's spectrogram.

FIG. 1A illustrates three angle views of a healthy person's spectrogram. The FIG. shows a two dimensional front view 150, a rotated three dimensional view 152 and a top down view 154 of a healthy person's acoustic spectrogram. The spectrogram comprises systoles 156 and diastoles 158. As can be seen, systole energy peaks center at approximately 22 Hz with frequencies ranging between 15 Hz to 30 Hz, having a timing of approximately 250 ms. The spectrogram shows a clear valley (low point) 160 followed by a diastole peak 158 having an energy height of approximately ⅓ of that of a systole peak 156.

In an embodiment, the present specification provides a system and method for diagnosing and guiding the treatment of a plurality of medical conditions/pathologies such as, but not limited to, large vessel occlusion (LVO) causing ischemic strokes, brain hemorrhages and migraines. These brain conditions differ from traumatic brain injuries (TBI) which present acutely, have a noticeable and direct cause, and involve brain swelling and bleeding with a gross insult on the brain, enabling a simple and clear diagnosis. The neurochronic pathologies listed above present differently from an acoustic perspective, relative to acoustic characteristics seen with TBI, wherein each condition has a vascular component and a resultant frequency expression resulting in a unique signature different from the signature produced by TBI. Furthermore, detection of non-traumatic brain conditions requires a careful determination of what vasculature structures are being detected to avoid detecting blood flow signatures through a patient's peripheral head vasculature, as opposed to blood flow signatures through the patient's brain.

The present specification is directed towards multiple embodiments. The following disclosure is provided in order to enable a person having ordinary skill in the art to practice the specification. Language used in this specification should not be interpreted as a general disavowal of any one specific embodiment or used to limit the claims beyond the meaning of the terms used therein. The general principles defined herein may be applied to other embodiments and applications without departing from the spirit and scope of the specification. Also, the terminology and phraseology used is for the purpose of describing exemplary embodiments and should not be considered limiting. Thus, the present specification is to be accorded the widest scope encompassing numerous alternatives, modifications and equivalents consistent with the principles and features disclosed. For purpose of clarity, details relating to technical material that is known in the technical fields related to the specification have not been described in detail so as not to unnecessarily obscure the present specification.

In the description and claims of the application, each of the words "comprise", "include", and "have", and forms thereof, are not necessarily limited to members in a list with which the words may be associated. It should be noted herein that any feature or component described in association with a specific embodiment may be used and implemented with any other embodiment unless clearly indicated otherwise.

In the specification the term "module" represents any digital or software component ranging from a discrete chip to a software algorithm the processing of which is distributed across multiple servers.

In an embodiment, the present specification provides a headset designed to be placed on a patient's head with at least one sensor, such as an accelerometer or microphone, positioned proximate to the patient's ear canal, such as within an ear cover of a headset. The headset is configured to passively detect the vibration of a fluid or elastic solid, generated from the cardiac cycle of the patient and, more specifically, from the pulsatile cerebral blood flow, as opposed to peripheral blood flow in the patient's head. In embodiments, the headset may be configured to passively detect acoustic frequencies. In various embodiments, the detected vibrations are compared with a predefined set of pre-recorded vibrations for determining whether the detected vibrations from the patient correspond to any of a plurality of medical conditions/pathologies such as, but not limited to, large vessel occlusion (LVO) and migraines.

In an embodiment, the one or more sensors passively receive the vibrations generated by the vasculature of the patient's brain. The vibrations (data) may be, in an embodiment, transmitted via Bluetooth from the headset to an Internet of Things (IOT) device that is configured to store algorithms configured to identify the pathology of interest, provide diagnostic data to the patient or transmit the diagnostic data to a cloud computing platform for analysis, and send the information back to the patient's smart device allowing the patient to obtain therapy for the pathology. In embodiments, data may be transmitted via any wired or wireless means. In embodiments, the headset may include a microchip or real-time operating system (RTOS).

In an embodiment, the vibrations generated by the pulsatile cerebral hemodynamics (cardiac cycle) of the patient is displayed as a spectrogram, which when compared with the spectrogram of a healthy person, demonstrates a shift in frequencies associated with one or more pathologies.

In an embodiment, the present specification provides a device with the electronic ability to switch between combinations of multiple acoustic and/or pressure-wave sensors. Said sensors are employed for measuring sound levels by measuring mechanical (or acoustic) waves corresponding to the pulsatile cerebral hemodynamics (cardiac cycle) of a patient. When an acoustic wave travels through the patient's body, it is influenced by the different material properties and obstacles it travels through. Any changes to the characteristics of this travelling path affect the velocity and/or amplitude of the wave. In embodiments, the device of the present specification translates said characteristics into a digital signal using transducers. In some embodiments, these changes are monitored by measuring the frequency or phase characteristics of the sensors employed. Acoustic wave sensors can be made to detect a range of properties by coating the sensors with materials that undergo changes in their mass, elasticity, or conductivity upon exposure to some physical or chemical stimulus. These sensors may be used as pressure, torque, shock, or force detectors if a stress that changes the dynamics of the propagating medium is applied thereon. In embodiments, the device of the present specification may employ a plurality of different types/configurations of surface acoustic wave (SAW) pressure sensors.

Figure 1B:
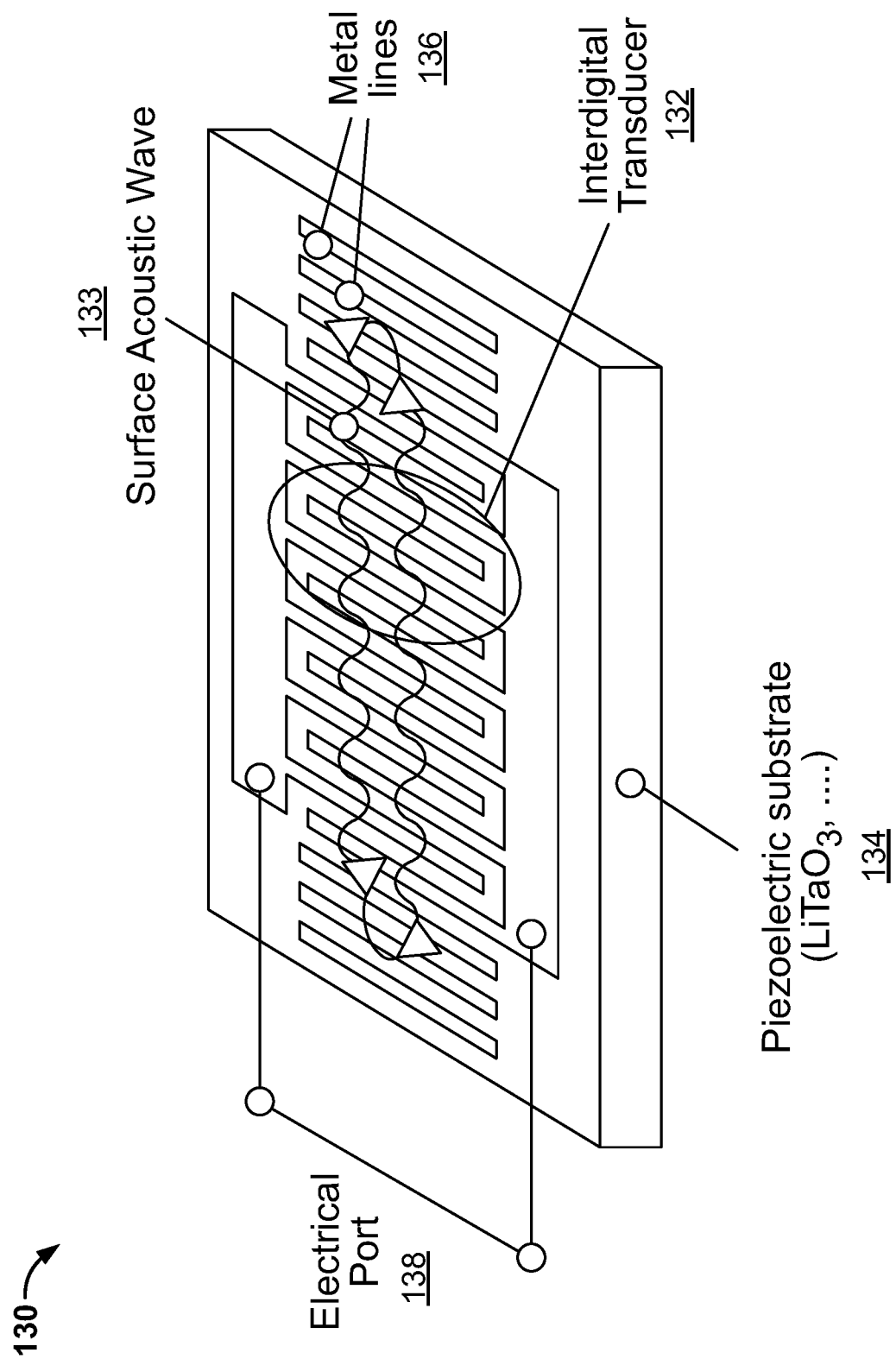
FIG. 1B illustrates an acoustic wave sensor comprising a piezoelectric substrate.

In an embodiment, the device of the present specification employs one or more acoustic wave sensors comprising a piezoelectric material to generate the acoustic wave. As is known piezoelectricity implies electricity resulting from pressure. FIG. 1B illustrates an acoustic wave sensor comprising a piezoelectric substrate. Acoustic wave sensor 130 comprises one or more inter digital transducers (IDT) 132 that can convert an incoming signal 133 (such as from the cardiac cycle of a patient) into a mechanical wave signal through a piezoelectric substrate 134. As shown, the transducers 132 are formed by interlocked electrodes 136 in a comb-structure and firstly convert an electrical signal into a mechanical wave and then convert said wave into an electrical signal output via electrical port 138 again. The distance between electrodes 136 determines the frequency of the wave and can be used to register torque or strain. In embodiments, the performance of acoustic wave sensors such as 130 may be changed by varying the length, width and position of the IDT 132. Piezoelectric acoustic wave sensors are relatively cheap, rugged, sensitive, reliable, and may be used passively (without a power source) and wirelessly.

In an embodiment, the present specification provides a device with electronically accessible combinations of acoustic and pressure-wave sensors placed over the following areas: ears, in front of the ears to more closely detect blood flow through the Superficial Temporal artery, behind the ears to more closely detect blood flow through the Maxillary artery, right and left sides of the neck to detect blood flow through the Common carotid and External carotid and Internal carotid arteries. Such a device may consist of two, four, six, eight, or nine separate sensors, two each for the right and left sides of previously mentioned areas and sensor number nine at the back of the neck.

In an embodiment, the present specification provides an algorithm designed to determine timing differences between the different sensors with the intention of determining the location of the issue represented as turbulent blood flow. In an embodiment, machine learning algorithms enhance the accuracy of the device and methods of the present specification, as more patient diagnostic data is processed for pattern-matching.

In an embodiment, an array of sensors is used in addition to the ear based sensor, for providing enhanced diagnostic information.

Figure 1C:
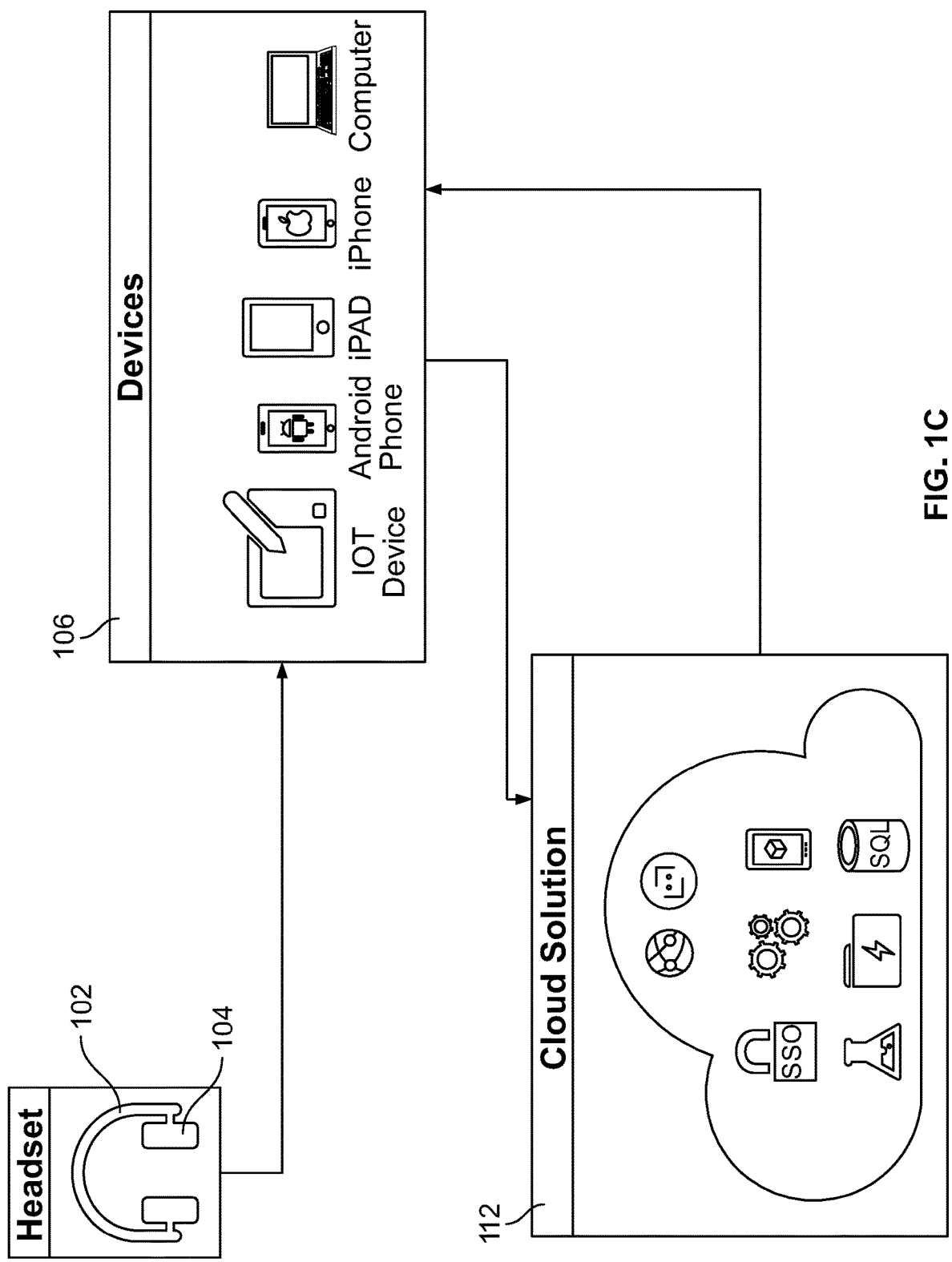
FIG. 1C is a block diagram illustrating a system of diagnosing and treating a plurality of pathologies in a patient, in accordance with an embodiment of the present specification.
Figure 1D:
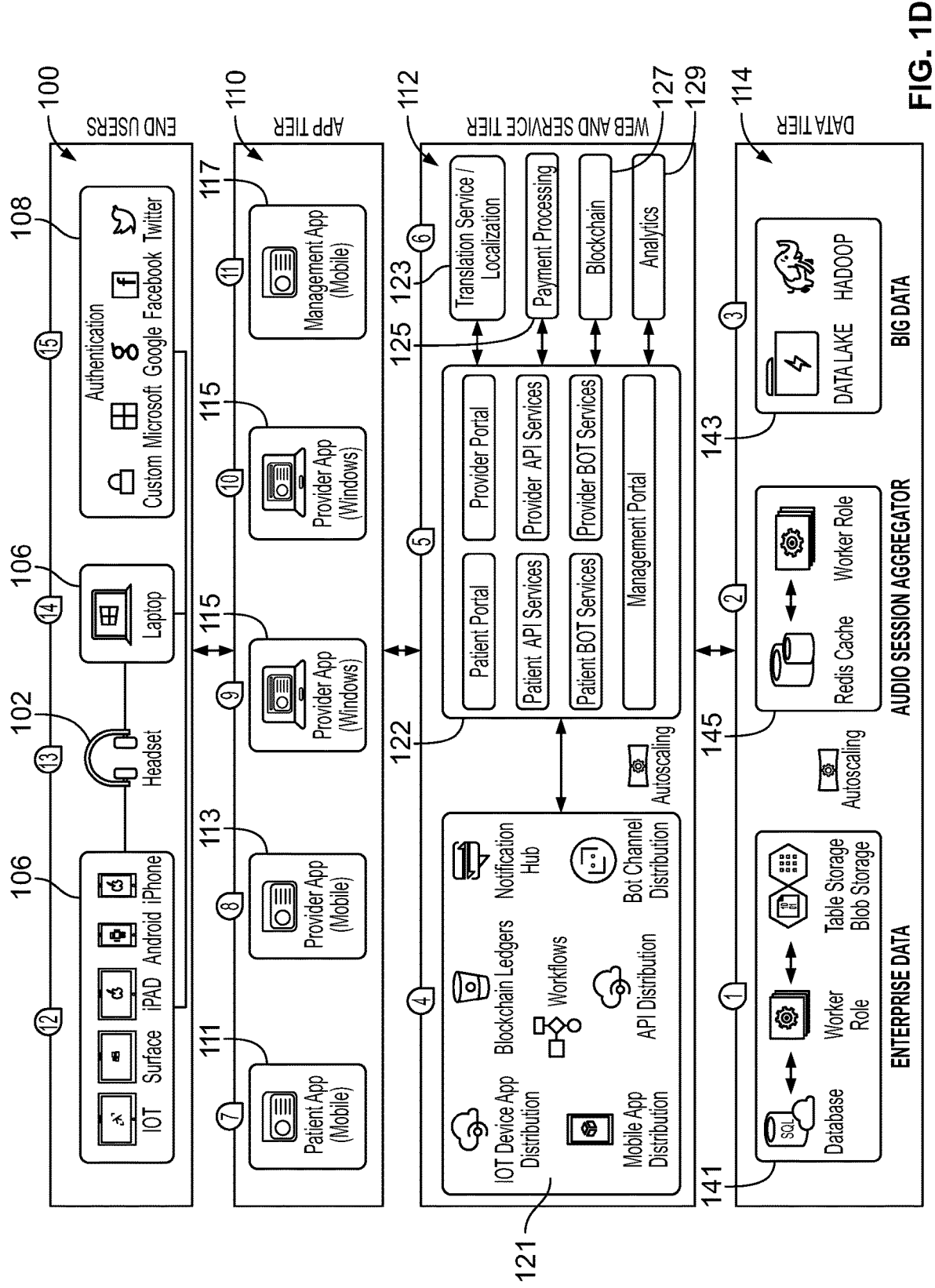
FIG. 1D is a block diagram illustrating a plurality of functional layers in the system of diagnosing and treating a plurality of pathologies in a patient, in accordance with an embodiment of the present specification.

FIG. 1C is a block diagram illustrating a system of diagnosing and treating a plurality of pathologies in a patient, in accordance with an embodiment of the present specification. FIG. 1D is a block diagram illustrating a plurality of functional layers in the system of diagnosing and treating a plurality of pathologies in a patient, in accordance with an embodiment of the present specification.

Referring to FIGS. 1C and 1D, the system comprises a headset 102 comprising two microphones 104, one microphone provided within each ear covering of the headset. The microphones 104 are configured to passively receive the vibrations generated by the vasculature of the brain of a patient wearing the headset 102. In an embodiment, the microphones (or pre-amplifiers, A/D converters, or blue tooth transmitters) 104 provide bi-hemispheric data and are designed to have a flat, consistent output to detect vibration in the range of 0-750 kHz. In an embodiment, the two ear coverings of the headset 102 have a parabolic design to enhance the capture of the vibrations generated by the patient and enhance the detected vibrations relative to external noise. In other embodiments, the ear coverings of the headset 102 may be designed in any suitable manner for detecting the vibrations from the patient's vasculature.

In another, less preferred embodiment, the headset 102 is a headset comprising a pre-amplifier, a frequency equalizer and a noise cancellation module. The headset comprises a signal generating apparatus configured to generate an acoustic or ultrasound signal into the brain. In preferred embodiments, the headset 102 is configured to passively receive the vibrations generated by the vasculature of the brain of a patient and does not include a signal generating apparatus, including any acoustic or ultrasound generating apparatus.

In various embodiments, the microphone 104 is accurate in the time and frequency domain and has a uniform polar response, a flat free-field frequency response, fast impulse response and is stable with respect to temperature changes.

In an embodiment, the headset 102 comprises an accelerometer to detect movement from a patient's head, and not just from the patient's vasculature. In an embodiment, the patient is held still by using head gear or one or more harnesses and multiple accelerometers are used to capture signals indicative of movement by the patient. Those captures signals can then be used to cancel out noise generated from movement. In various embodiments, the site of the transducer is distant from muscles and skin that are activated and can move during the examination.

In an embodiment, the headset 102 comprises a signal quality indicator (SQI) to indicate the quality of a signal prior to a test being run, a light emitting diode (LED) to indicate that the headset is on and a light array to indicate a level of battery charge. In an embodiment, the headset 102 may be coupled with a plurality of user computing devices 106 such as, but not limited to Internet of Things (IoT) devices, mobile phones, tablets, and computers 106 via a wireless connection such as, but not limited, to a Wi-Fi network, cellular, or a Bluetooth connection. In embodiments, the user devices 106 enable display of data captured by the headset 102 and other notifications to the user using the headset. In embodiments, the user may be required to provide authentication information by using one of a plurality of authentication methods comprising custom authentication, or authentication methods provided by service providers 108 such as, but not limited to Google®, Facebook®, and Twitter®. In some embodiments, the headset 102, user devices 106, and service providers are grouped in an end user's tier 100.

In embodiments, a plurality of software applications 110 executing on the user devices 106 enable connection of the user devices 106 with the headset 102 as well as with a cloud solution computing platform (web and service tier) 112 via a wireless connection such as, but not limited, to a Wi-Fi network, cellular, or a Bluetooth connection. The applications 110 may comprise patient mobile applications 111, service provider mobile applications 113, service provider Windows® applications 115, and management applications 117, which also enable transfer and display of information captured/processed by the headset 102 and the cloud solution computing platform 112.

In various embodiments, the cloud solution computing platform (web and service tier) 112 comprises a management portal 122, a workflow module 121, and a set of service or storage modules, including, but not limited to, a translation service/localization module 123, a payment processing module 125, a block-chain module 127, and an analytics module 129. In embodiments, the management portal 122 comprises a patient portal, patient API services, patient BOT services, a provider portal, provider API service, and provider BOT services. The management portal 122 is in data communication with the workflow module 121, which controls IOT device application distribution, block-chain ledgers, a notification hub, mobile application distribution, API distribution, and BOT channel distribution. The management portal 122 is also in data communication with each of the translation service/localization module 123, payment processing module 125, block-chain module 127, and analytics module 129, providing patients and providers access to these modules via the patient portal and provider portal, for various services.

The vibrations detected by the microphones 104 are analyzed by a signal analyzer comprising at least one processor and a plurality of programmatic instructions stored in a memory, where the plurality of programmatic instructions include DSP, and machine learning, Artificial Intelligence, deep learning, neural networks (NN) and pattern recognition based algorithms, such as neural networks and artificial intelligence systems, in order to detect one or more of a set of pre-defined pathologies present in the detected vibrations of the patient. Preferably, pre-recorded acoustic patterns and specific frequencies unique to each kind of pathology are stored in one or more data tiers 114 coupled with the signal analyzer, which may be executed in a cloud solution computing platform 112. The data tier 114 comprises a plurality of databases, including enterprises databases 141, big data 143, and/or an audio session aggregator 145 that receives, stores, and/or catalogs signal signatures, spectrograms, frequency windows, and/or data patterns, each of which is indicative of a different pathology type.

Each pathology generates a unique acoustic pattern and specific frequency that enables identification of the pathology. For example, migraines generate (depicted by a spectrogram) a unique frequency pattern associated with the migraine. Using DSP, machine learning, and or AI pattern recognition based algorithms, the stroke severity levels may be identified. In an embodiment, data describing a pathology collected from each case is used to expand the database, which further enhances the quality/accuracy of the AI algorithms. In an embodiment, each patient's data is also sent to a secure website which provides patients an encrypted/password protected access to their data and history.

In an embodiment, the cloud solution computing platform 112 is coupled with one or more user devices 106 via a wireless connection such as, but not limited, to a Wi-Fi network, or a Bluetooth connection. In various embodiments, the user devices 106 comprise a graphical user interface (GUI) for displaying at least a diagnosis of the patient's condition. In an embodiment, the GUI displays one or more pathologies determined by the AI algorithms. In an embodiment, the user devices 106 also receive packets of diagnostic information from the cloud solution computing platform 112, to provide information on the severity of the pathology, and display the information as a quantitative value.

Figure 2:
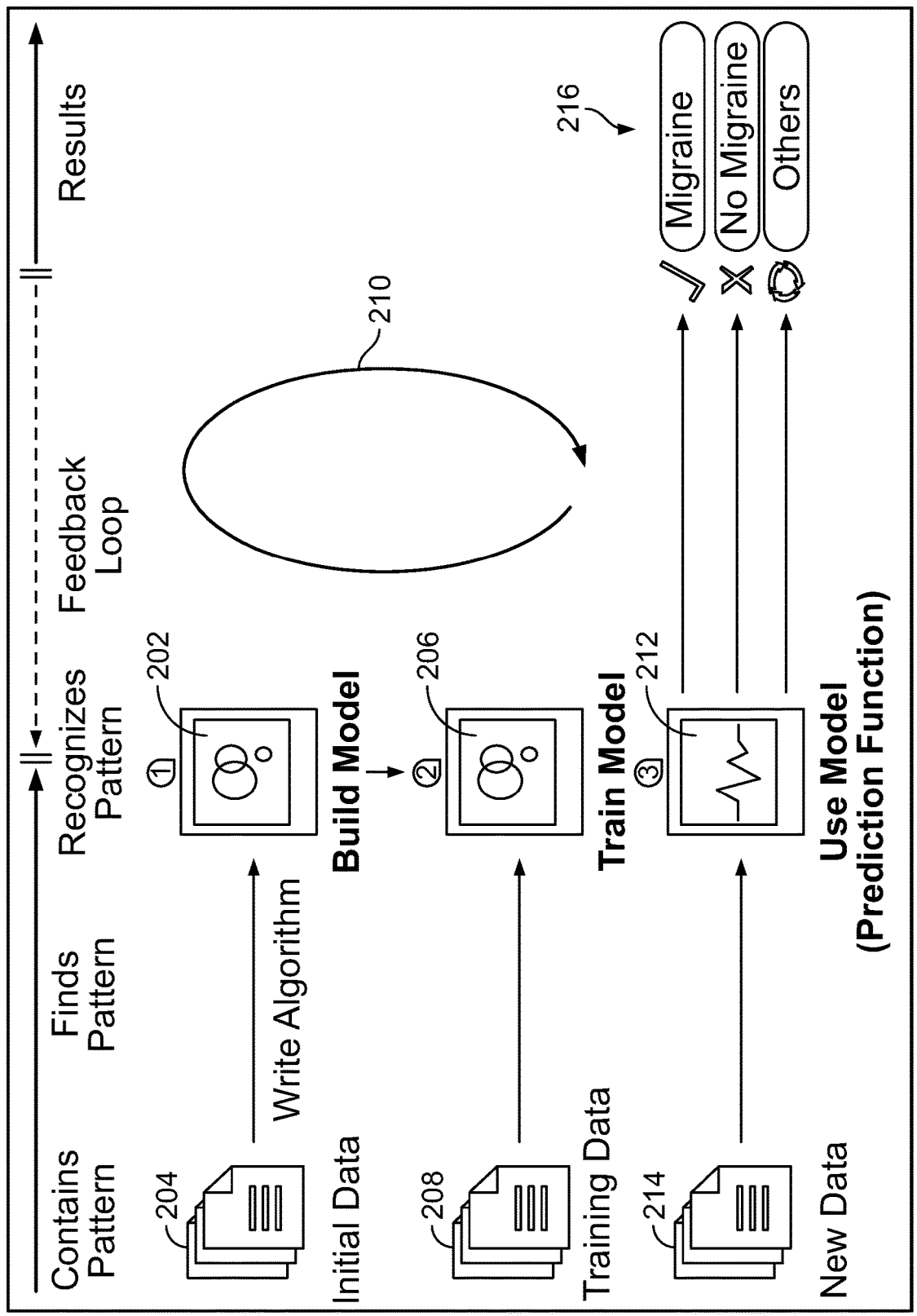
FIG. 2 is a block diagram illustrating a process of diagnosing pathologies by using artificial intelligence (AI) based algorithms, in accordance with an embodiment of the present specification.

FIG. 2 is a block diagram illustrating a process of diagnosing pathologies such as a stroke by using a signal analyzer 202 configured to process initial data 204 comprising patterns defining a pathology for identifying said patterns by comparison with one or more predefined recorded patterns. The build model 202 is developed using a training model 206 by employing training data 208, as well as by providing the results of the build model 202 as a feedback 210 to the training model 206. The feedback 210 enables the training model 206 to learn to recognize diagnostic patterns and develop into a use model 212. The use model 212 identifies diagnostic patterns, in any new input data 214, by comparison, and provides results 216 conveying if a pathology such as 'migraine' or IVO' is present in the data 214 or not.

Figure 3:
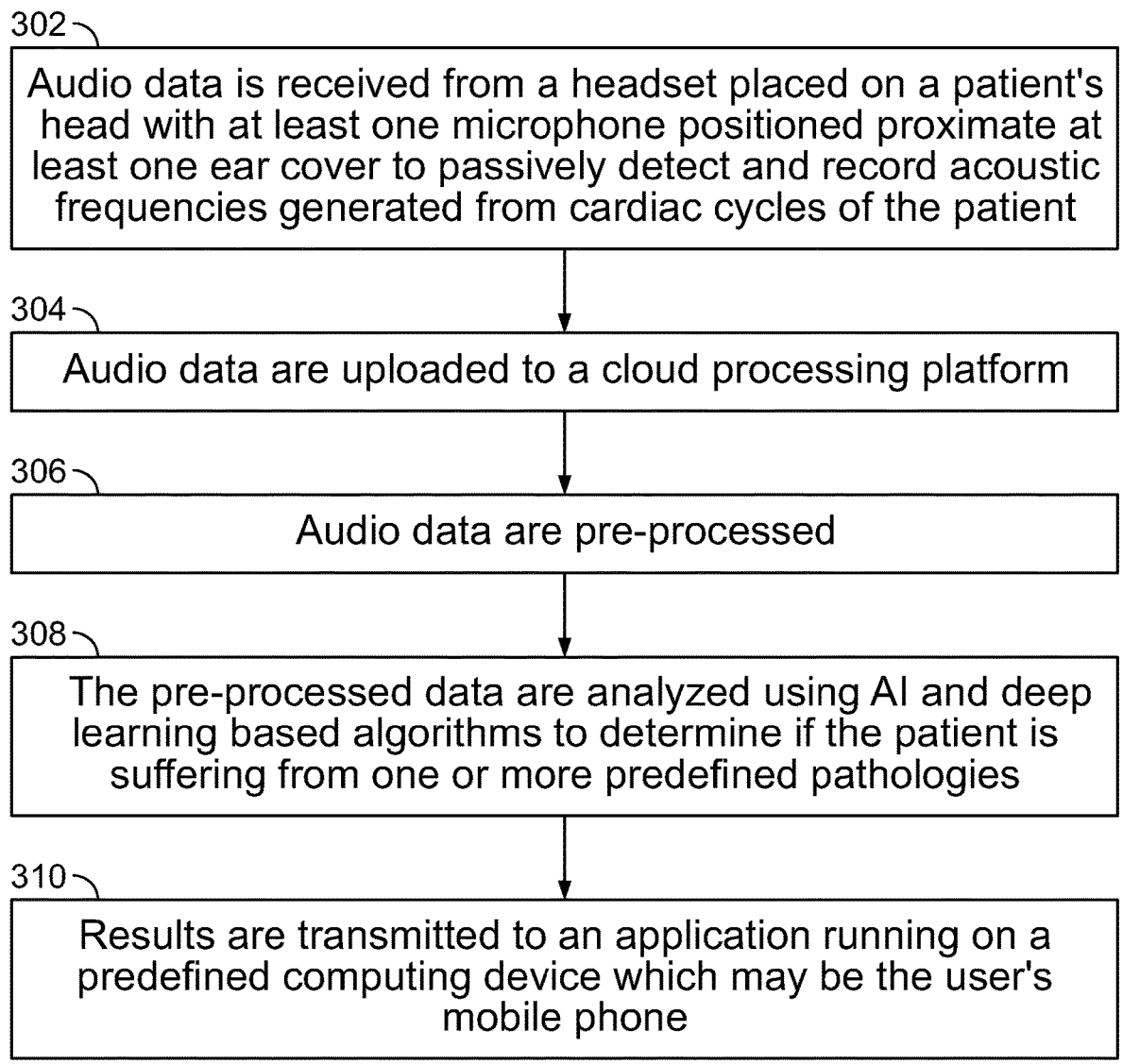
FIG. 3 is a flow diagram illustrating a data flow during the process of diagnosing a pathology in a patient, in accordance with an embodiment of the present specification.

FIG. 3 is a flow diagram illustrating a data flow during the process of diagnosing a pathology in a patient, in accordance with an embodiment of the present specification. At step 302 audio data is received from a headset placed on a patient's head with at least one accelerometer or microphone positioned within 1 foot of the patient's ear. In a preferred embodiment, at least one microphone is positioned within each ear cover of the headset to passively detect and record vibrations generated by blood flow within a patient's brain from cardiac cycles of the patient.

At step 304, the captured audio data is digitized and transmitted to a cloud processing platform. In an embodiment, the audio data is stored in a mobile application, which in turn uploads the data to the cloud processing platform. Next the data is pre-processed at step 306. In an embodiment, the audio data is cleaned by applying noise reduction techniques to obtain clean audio patient data. In an alternate embodiment, the audio data is processed at a local device and then uploaded to a cloud platform.

In an embodiment, audio data may be processed via a beamforming technique. In this technique, two microphones would be employed in each ear, forming a beam of interest. In an embodiment, beamforming can be used to remove noise by attenuating all noises in the environment and focusing on the narrow beam pointing towards the ear canal to extract the signal of interest. In this embodiment, noise is not removed from the signal, rather any signal that falls outside of the beam of interest, and therefore any signal that is not coming directly from the ear canal, would be cancelled.

Figure 4A:
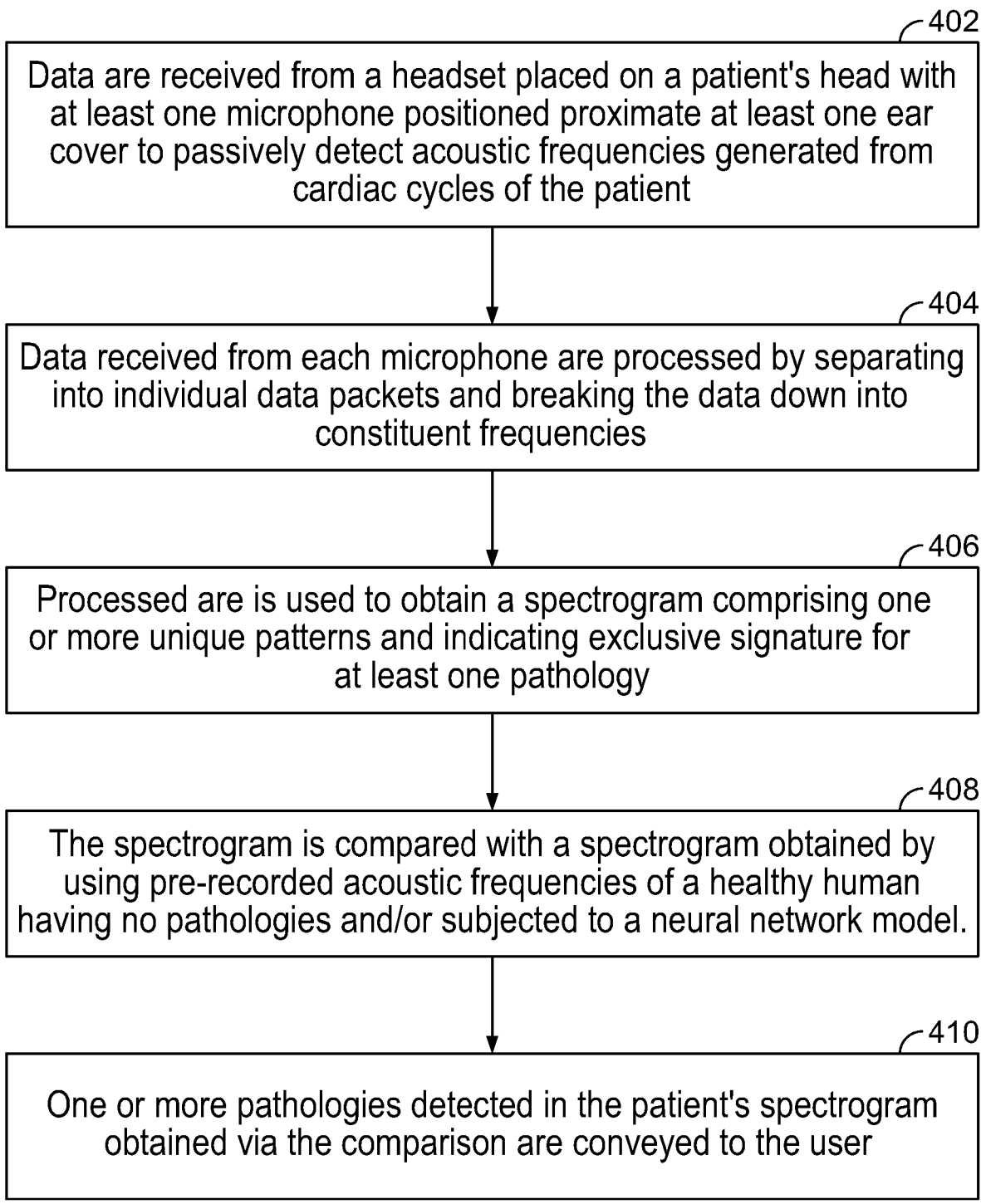
FIG. 4A is a flow chart illustrating a method of diagnosing and treating a plurality of pathologies in a patient, in accordance with an embodiment of the present specification.
Figure 4B:
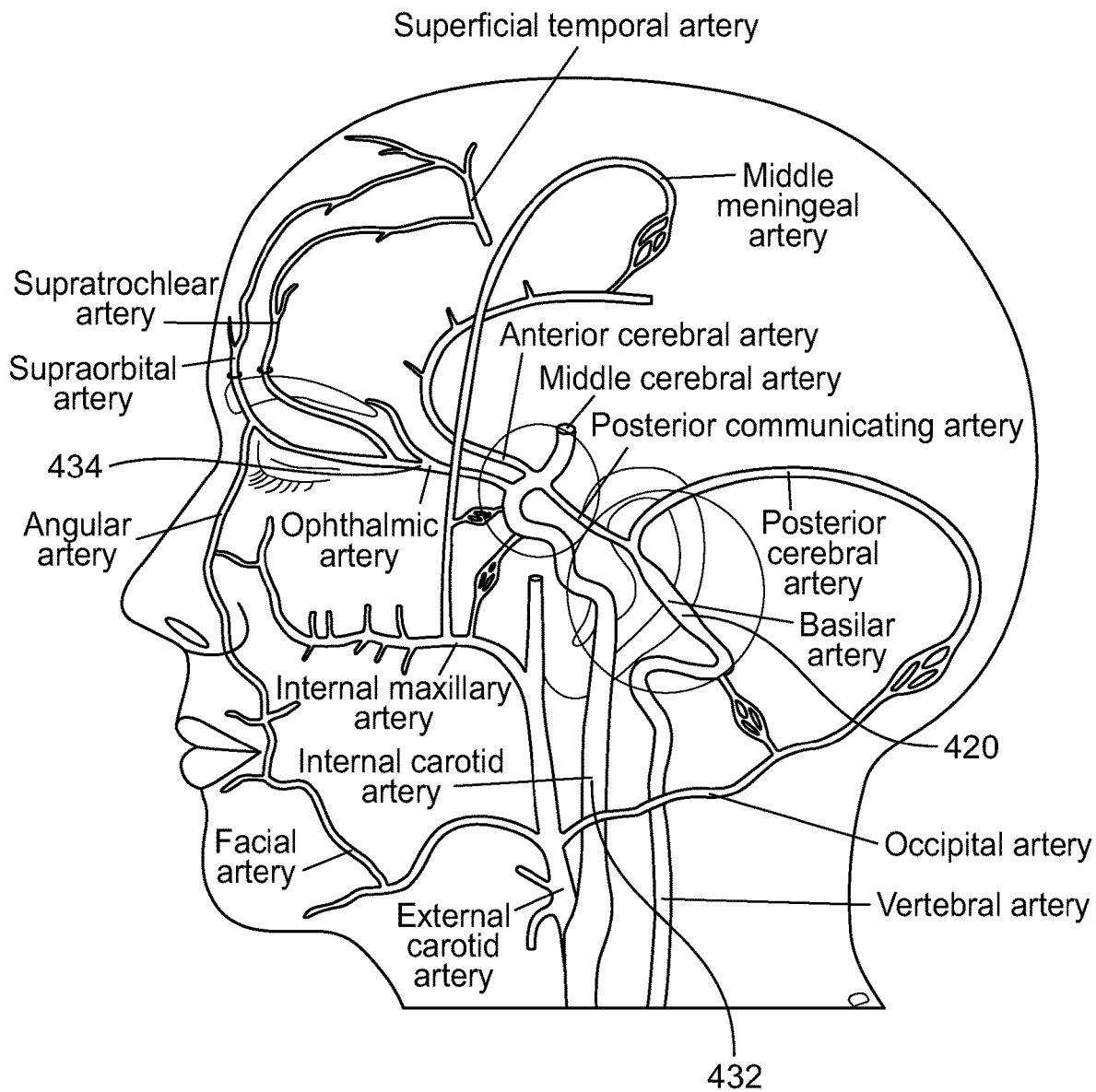
FIG. 4B illustrates flow of blood through arteries in a person's head.
Figure 4C:
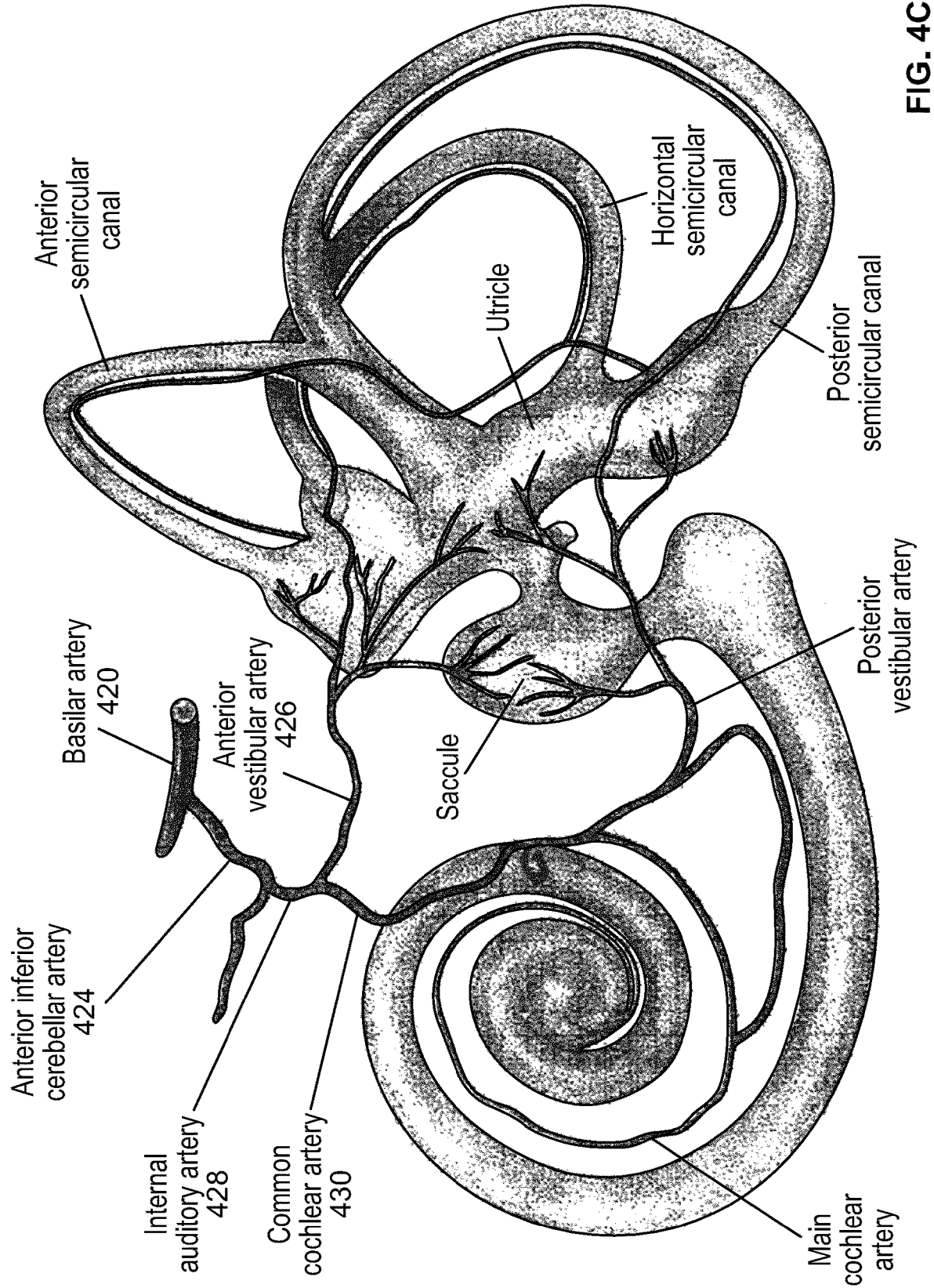
FIG. 4C is diagrammatic representation of the arteries carrying blood to a person's head.
Figure 4H:
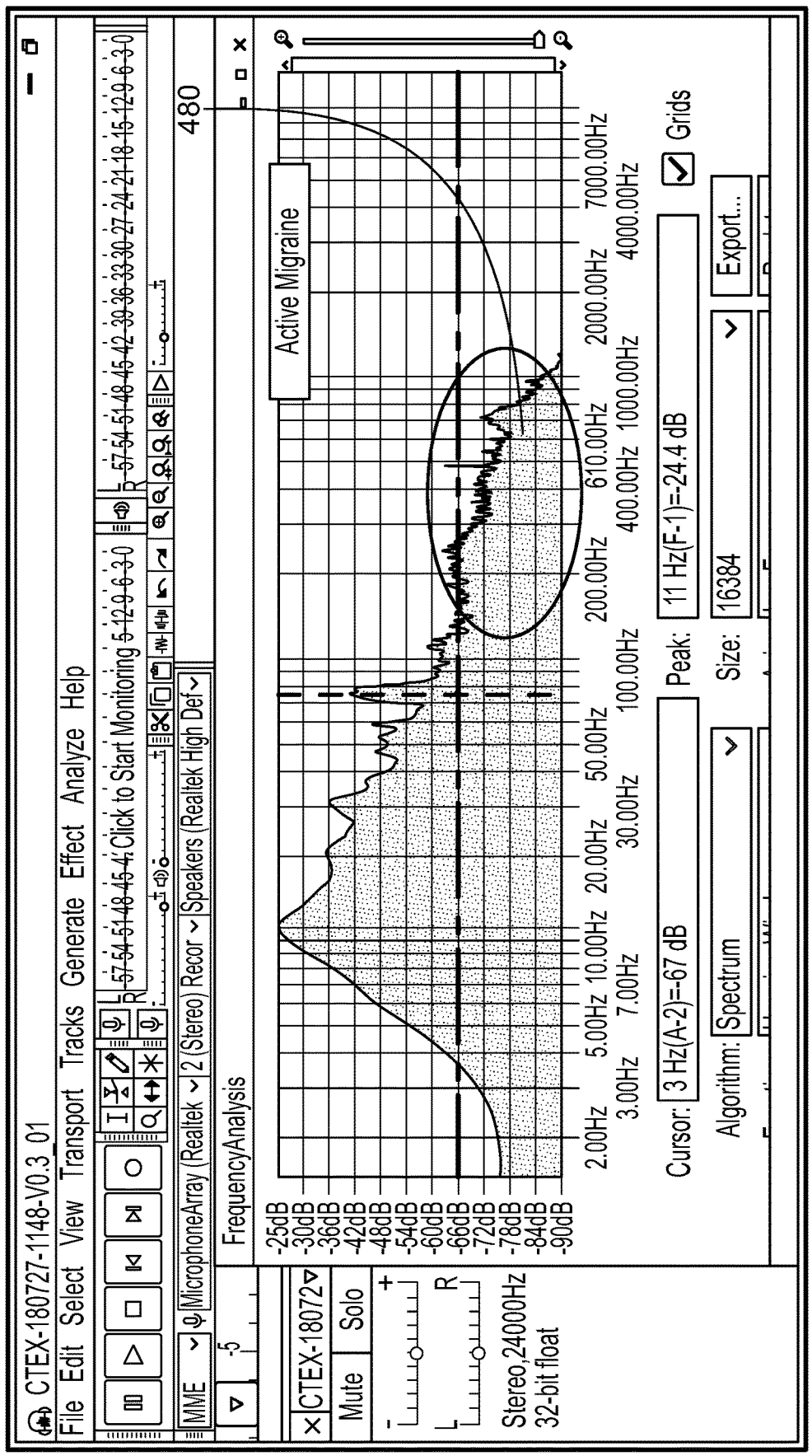
FIG. 4H is a graphical representation of a unique data signature of a person suffering from migraine as compared to that of a person not suffering from migraine as determined over a frequency range, in accordance with an embodiment of the present specification.
Figure 4H:
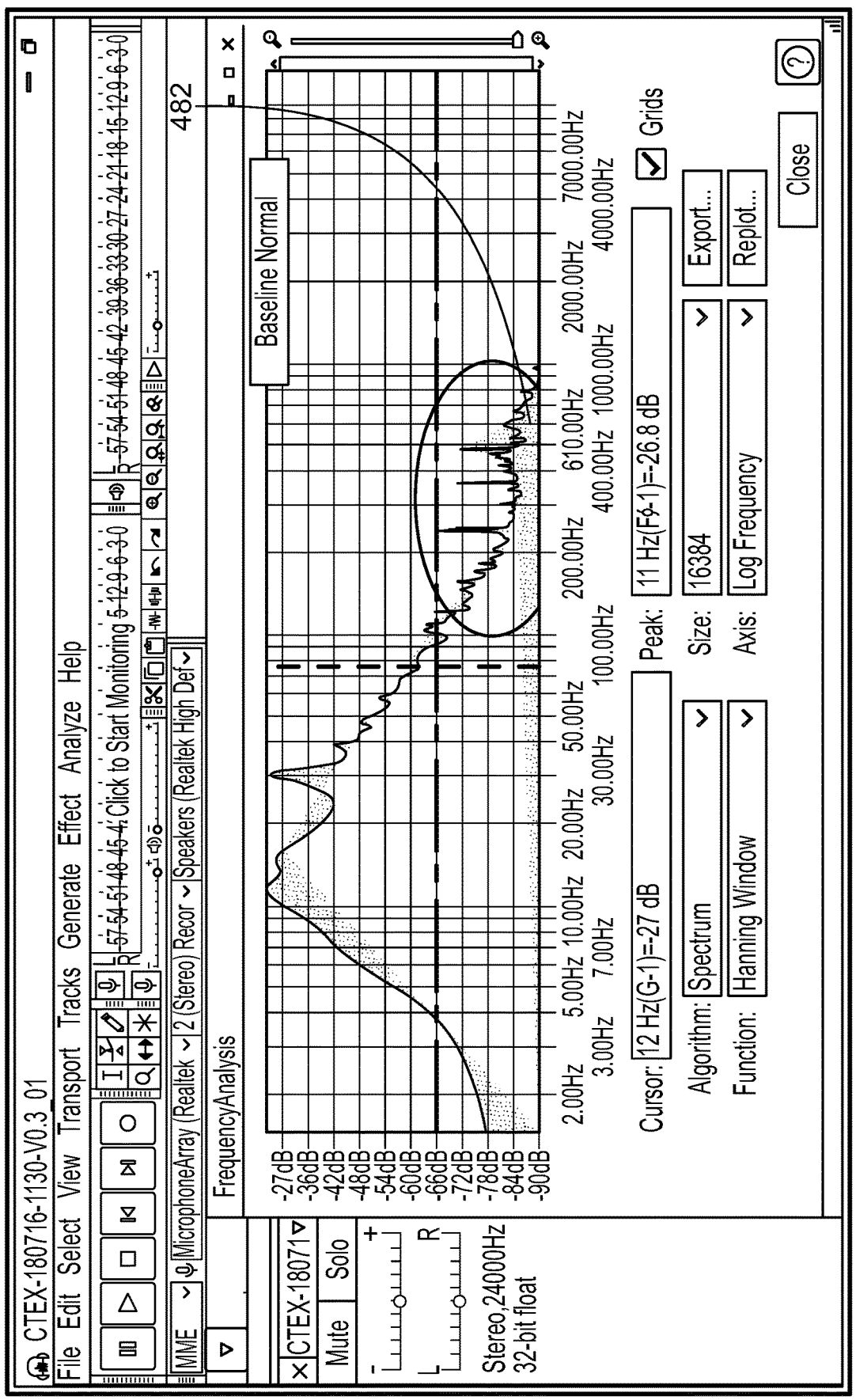
Figure 4I:
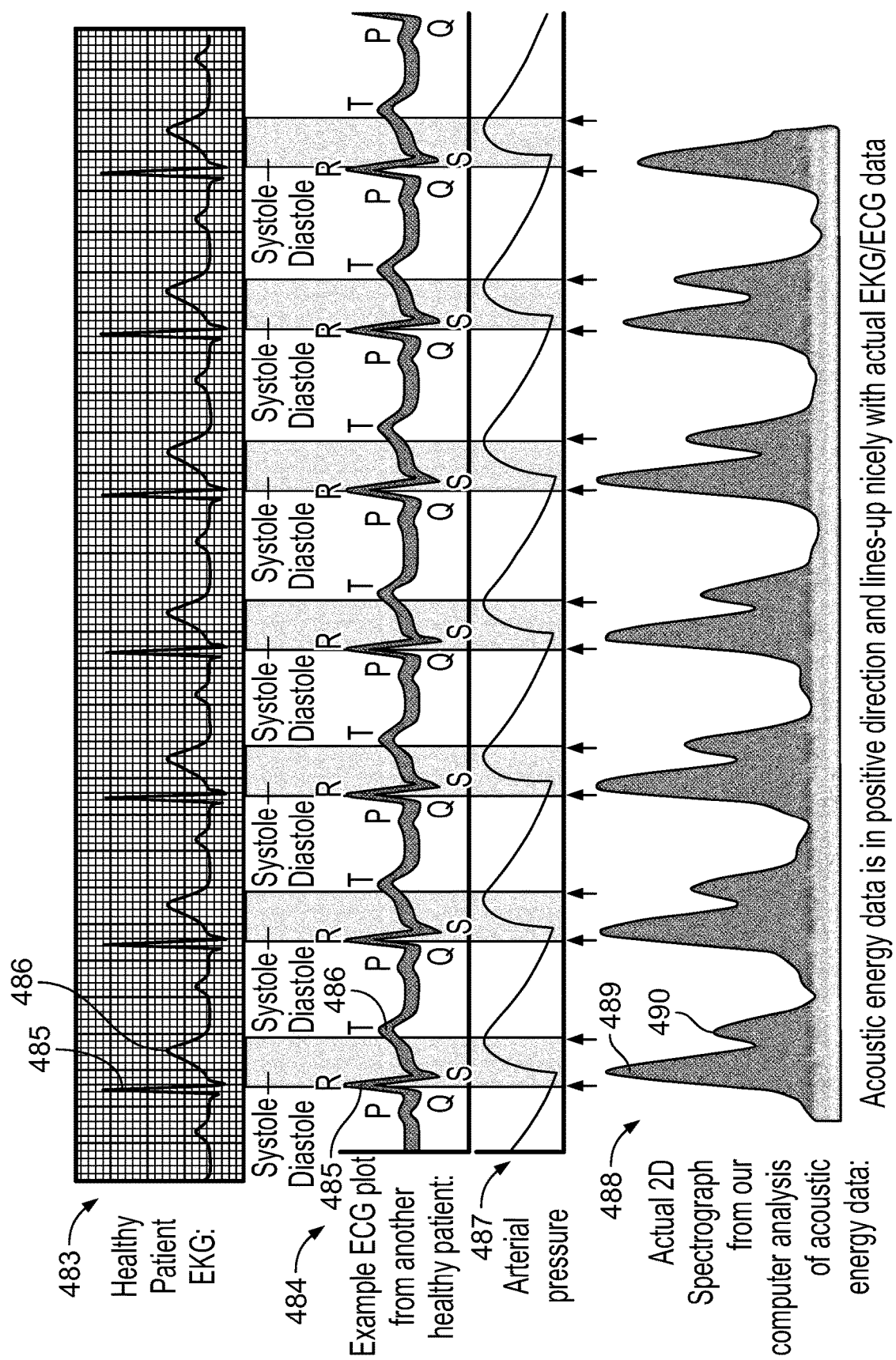
FIG. 4I illustrates EKG graphs and corresponding spectrogram of a healthy person, in accordance with an embodiment of the present specification.

The cleaned or scrubbed audio data is then processed to obtain spectrogram images, such as shown in FIG. 1A, FIGS. 4H and 4I. At step 308 the pre-processed data is analyzed using AI and deep learning-based algorithms to determine if the patient is suffering from one or more predefined pathologies. At step 310 the results are transmitted to an application running on a predefined computing device which may be the user's mobile phone.

The method of determining and displaying pathologies corresponding to a patient's acoustic data is further described with reference to FIG. 4A. FIG. 4A is a flow chart illustrating a method of diagnosing and treating a plurality of pathologies in a patient, in accordance with an embodiment of the present specification. At step 402 data is received from a headset placed on a patient's head with one microphone positioned within each ear cover to passively detect vibrations generated from cardiac cycles of the patient. In an embodiment, the microphones passively receive vibrations generated by the vasculature of the brain. In an embodiment, the acoustic data comprises signals having a frequency above 150 Hz. In some embodiments, the acoustic data comprises signals having a frequency range between 20 Hz and 200 Hz. In other embodiments, the acoustic data comprises signals having a frequency range greater than 200 Hz. In some embodiments, the acoustic data comprises signals having a frequency range between 200 Hz and 750 Hz. In various embodiments, signals are analyzed in the frequency domain and as a function of time.

At step 404 the data received from each microphone is processed. In an embodiment, the received data is separated into individual data packets and decomposed into constituent frequencies using any known data transformation algorithm such as but not limited to Fourier transform, wherein the frequencies and the amplitude of the received vibrations are examined as a function of time. In various embodiments the data received from each microphone may be used to generate unique patterns and features that may indicate an exclusive signature for different pathologies. The vibrations obtained from the cardiac cycle (diastole & systole) range from a normal baseline of approximately 15-20 Hz and shift further into the spectrum to approximately 30 to 80 Hz, depending on the pathology being assessed.

At step 406 the processed data is used to obtain a spectrogram comprising a unique pattern and indicating an exclusive signature for a pathology. In an embodiment, the processed data comprises predefined frames of audio signals having frequencies ranging from approximately 150 Hz to 1000 Hz. In an embodiment, a sum of all energies within said range is computed with respect to each frame to obtain a spectrogram of the captured data.

At step 408 the spectrogram is compared with a spectrogram obtained by using pre-recorded vibrations of a healthy human having no pathologies. In various embodiments, the patient's spectrogram may be compared with a plurality of pre-recorded spectrograms for determining if any of a set of pre-defined pathologies are present in the patient's acoustic data. In an embodiment, the time, frequency and amplitude of vibrations generated by the vasculature of the brain of the patient are compared with those of a healthy human or of humans with specific pathologies, such as an LVO or a migraine.

In various embodiments the comparison of the patient's spectrogram with other spectrograms to obtain if the patient suffers from any of a plurality of pre-defined pathologies is achieved in the signal analyzer by using artificial intelligence (AI), machine learning, trained neural networks, or pattern recognition based algorithms. In an embodiment, distinctive acoustic patterns and frequencies generated from a pathology, if present in a patient's spectrogram, are identified by using AI, machine learning and pattern recognition-based algorithms.

At step 410 one or more pathologies detected in the patient's spectrogram are displayed to the user via a GUI running on a computing device. In an embodiment, the signal analyzer detects the features of the waveform and provides a qualitative and quantitative diagnostic output to assess if the patient has the pathology or not. In an embodiment, the qualitative output is a simple stop light where green is no pathology present, yellow is pathology below a threshold level present and red is pathology above a threshold present. In other embodiments, a quantitative number, on a scale of 1 to 10 is displayed to describe the severity of the detected pathology.

In various embodiments, cerebral vasculature response (vasodilation and vasoconstriction), byproducts of an underlying LVO condition, can be measured and identified. FIG. 4B illustrates flow of blood through arteries in a person's head. FIG. 4C is diagrammatic representation of the arteries carrying blood to a person's head. Since the human heart pumps blood bilaterally to the brain through the carotid arteries, pumping of the heart, along with asymmetric blood flow, pulses the blood through the cerebral blood vessels. In various embodiments, cerebral vasculature response (vasodilation and vasoconstriction), are measured via such cerebral arteries, and identified.

Referring to FIGS. 4B and 4C, a patient's cerebral vasculature response may be measured via the basilar artery 420, the anterior inferior cerebellar artery 424, the anterior vestibular artery 426, the internal auditory artery 428, the common cochlear artery 430, the internal carotid artery 432, the ophthalmic artery 434, or the branches of any of the aforementioned arteries ("Target Cerebral Vasculature"). In embodiments, cerebral vasculature response may be measured via said arteries by placing a sensor within the ear canal of the person or within a predefined distance from a wall of one or more of the Target Cerebral Vasculature. In one embodiment, the predefined distance is within 0 mm to 20 mm, preferably within 0 mm to 10 mm, and more preferably within 0 mm to 5 mm, or any increments therein.

In contrast, it is preferred to avoid placing sensors in locations that would result in the detection of peripheral blood flow, which is not indicative of the actual cerebral vasculature. Such locations may include above the zygoma which is the bony arch of the cheek formed by connection of the zygomatic and temporal bones of the person, the external carotid artery, the internal maxillary artery, the facial artery, the occipital artery or the branches of any of the aforementioned arteries ("Non-Target Peripheral Vasculature"). In particular, it is preferable to place a sensor outside of a predefined distance from a wall of one or more of the Non-Target Peripheral Vasculature. In one embodiment, the predefined distance is outside of 20 mm, preferably outside of 10 mm, more preferably outside of 5 mm, even more preferably outside of 2 mm, or any increments therein.

Therefore, it is important to position the sensors in a location and configuration where the primary signals being received by the sensors are indicative of the acoustic properties of blood flow through the Target Vasculature and not indicative of the acoustic properties of blood flow through the Non-Target Vasculature. In one embodiment, one, more than one, or all of the sensors are physically positioned closer to at least one of the Target Cerebral Vasculature relative to each of the Non-Target Peripheral Vasculature. In one embodiment, one, more than one, or all of the sensors are physically positioned within 5 mm of a wall of at least one of the Target Cerebral Vasculature and further than 5 mm from each of the Non-Target Peripheral Vasculature. In one embodiment, one, more than one, or all of the sensors are physically positioned within 10 mm of at least one of the Target Cerebral Vasculature and further than 10 mm from each of the Non-Target Peripheral Vasculature. In one embodiment, one, more than one, or all of the sensors are physically positioned within 0 mm to 5 mm of at least one of the Target Cerebral Vasculature and further than 5 mm from each of the Non-Target Peripheral Vasculature.

In an embodiment, the pulsation of blood through artery walls is picked up by sensitive microphones placed near the ear canal. FIG. 4D illustrates microphones 440 placed near the ear canal 445 of a person, in accordance with an embodiment of the present specification. FIG. 4E illustrates scanning regions 450 of acoustic sensors within the brain of a person, in accordance with an embodiment of the present specification.

FIG. 4F illustrates blood flow from an internal carotid artery 462 to a left part 464 of a person's brain via an anterior cerebral artery 466 and to a right part 468 of the person's brain via a middle cerebral artery 470. FIG. 4G illustrates an occluded middle cerebral artery restricting the flow of blood to the right part of the person's brain shown in FIG. 4F. As can be seen the middle cerebral artery 470 is occluded in FIG. 4G preventing blood flow into the right part 468 of the person's brain. The condition shown in FIG. 4G leads to the person suffering from an Ischemic stroke. Stenosis in an artery refers to narrowing of the artery due to an occlusion. As provided in the book '*Clinical Methods: The History, Physical, and Laboratory Examinations. 3rd edition*' (incorporated herein by reference): "As stenosis/narrowing of artery increases, potential energy (pressure) proximal to the stenosis changes to increasing kinetic energy (velocity) within the stenosis. With increasing flow velocity, laminar flow through a stenosis eventually changes to turbulent flow, producing vibrations and a bruit. Thus, velocity through the stenotic segment of the artery and the subsequent character of the bruit depend on the degree of stenosis and the resulting pressure gradient. If only the degree of stenosis is considered, the auscultatory quality and timing of the resultant bruit follow directly. A soft early systolic bruit is noted with a lumen diameter of 50%. As the obstruction increases to 60%, the bruit becomes high pitched, more intense, and holosystolic. At 70 to 80% diameter reduction, a pressure gradient may remain even during diastole, and the bruit is auscultated in both systole and early diastole." Hence, in various embodiments, the occluded artery leads to rigid expansion and loosening of the artery walls, which in turn results in the cerebral vasculature having distinct audio properties.

In embodiments, the present specification provides a method of capturing the cerebral vasculature (via headphones, as explained above) preparing an audio spectrogram, comparing the audio properties with stored spectrograms of healthy persons and persons suffering from ischemic stroke to diagnose the occurrence of an LVO or stroke.

It has been observed that pulsation of blood through the cerebral vasculature is impacted by migraine in a predictable way. Hence, in an embodiment, the vibrations from patients suffering from migraine are analyzed by using the signal analyzer, classified, and the results provided to the clinician to diagnose an active migraine. FIG. 4H is a graphical representation of a unique data signature of a person suffering from migraine as compared to that of a person not suffering from migraine as determined over a frequency range, in accordance with an embodiment of the present specification. Plot 480 depicts the data obtained from a person suffering from active migraine while plot 482 depicts the data obtained from a person with no migraine symptoms, wherein the data corresponds to a frequency greater than 200 Hz. FIG. 4I illustrates EKG graphs and corresponding spectrogram of a healthy person, in accordance with an embodiment of the present specification. Graph 483 depicts the EKG reading of a first healthy person, while graph 484 depicts the EKG reading of a second healthy person. Both the graphs 483, 484 comprise systole 485 and diastole 486 peaks. Graph 487 depicts arterial pressure corresponding to graphs 483, 484. Spectrogram 488 is a two dimensional spectrogram obtained by analyzing acoustic arterial data of a healthy person. As can be seen, systole 489 and diastole 490 of the spectrogram 488 align with the systole 485 and diastole 486 peaks of the EKG graphs 483, 484 and the arterial pressure graph 487.

Referring back to FIG. 1D, in some embodiments, the plurality of software applications 110 includes an assessment application, module or engine that executes on the user devices 106 corresponding to medical personnel or clinicians such as, for example, EMS (Emergency Medical Services) personnel and CSC (Comprehensive Stroke Center) personnel. In embodiments, the assessment application executes a plurality of instructions or programmatic code to direct a medical personnel or clinician through a plurality of generated GUIs (Graphical User Interfaces) where each GUI presents input areas configured to receive information from the medical personnel or clinician and output areas configured to display information to the medical personnel or clinician.

When executed on a medical personnel's device, the assessment application is configured to enable the medical personnel to sign in with his unique ID, pair or synchronize with a patient's headset and then implement a triage process that takes the medical personnel through a plurality of questions, using one or more GUIs, in order to assess if the patient is suffering from LVO/stroke or migraine. As a non-limiting example, in some embodiments, the plurality of questions includes clinical information related to: whether the patient being assessed is new or a returning patient, number of headaches experienced each month, duration of the headaches, list of medication prescribed, intensity of the headaches or pain level, specific site or location of the headaches, tests performed (for example, MRI, CT, etc.), blood pressure measurements, and pulse rate. In embodiments, the assessment application is configured to receive data including blood work data, historical treatment data, physical exam data, or imaging data of the patient. For example, the assessment application may be configured to receive complete blood count information, including red blood cell, white blood cell, hemoglobin, hematocrit, and platelet data. The assessment application may be configured to receive electrolyte information, including sodium, chloride, potassium, and bicarbonate data. The assessment application may be configured to received historical treatment data including information from previous office visits, surgeries and procedures, and prescription data. The assessment application may be configured to receive physical exam data, including weight, height, blood pressure, temperature, pulse rate, and findings upon physical exam data. The assessment application may be configured to receive imaging data including X-ray, ultrasound, CT, Mill, and positron-emission tomography (PET) data.

Figure 5A:
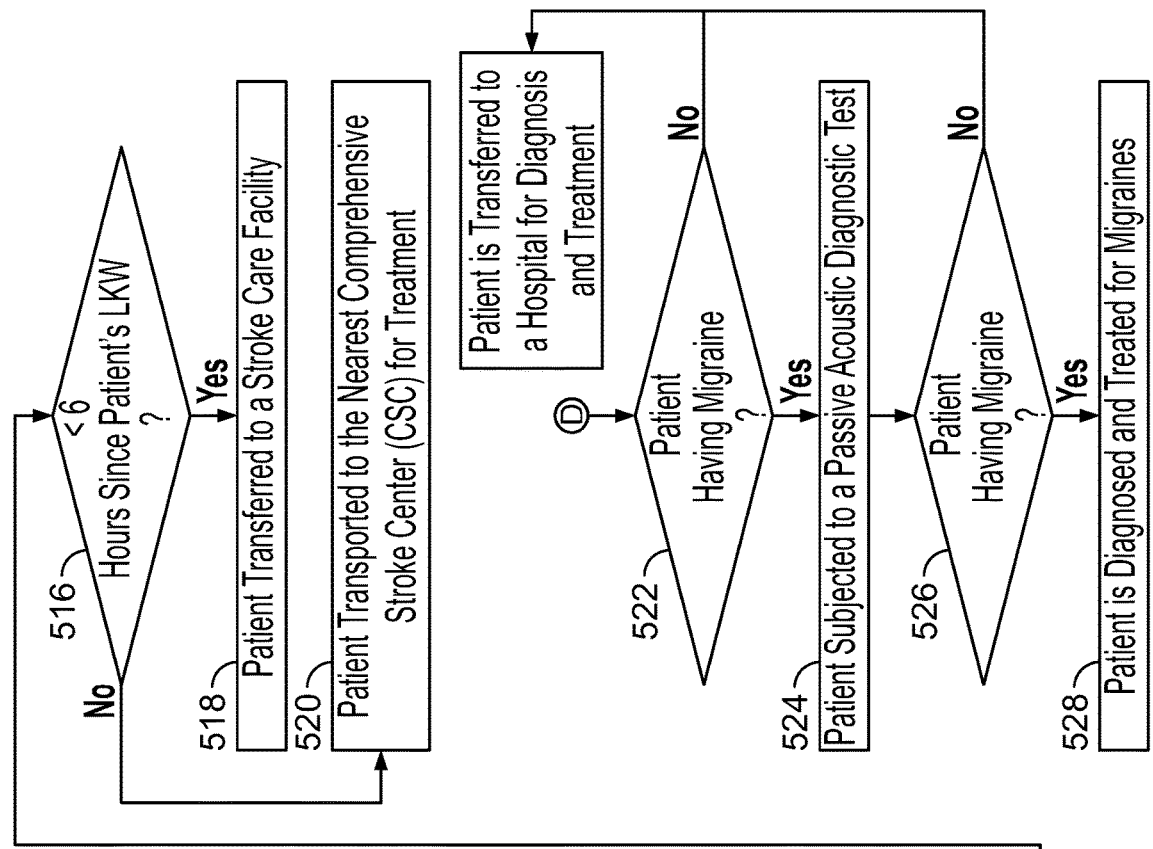
FIG. 5A is a flowchart illustrating a method of responding to a patient presenting with complaints of stroke or migraine by Emergency Medical Services (EMS), in accordance with an embodiment of the present specification.
Figure 5A:
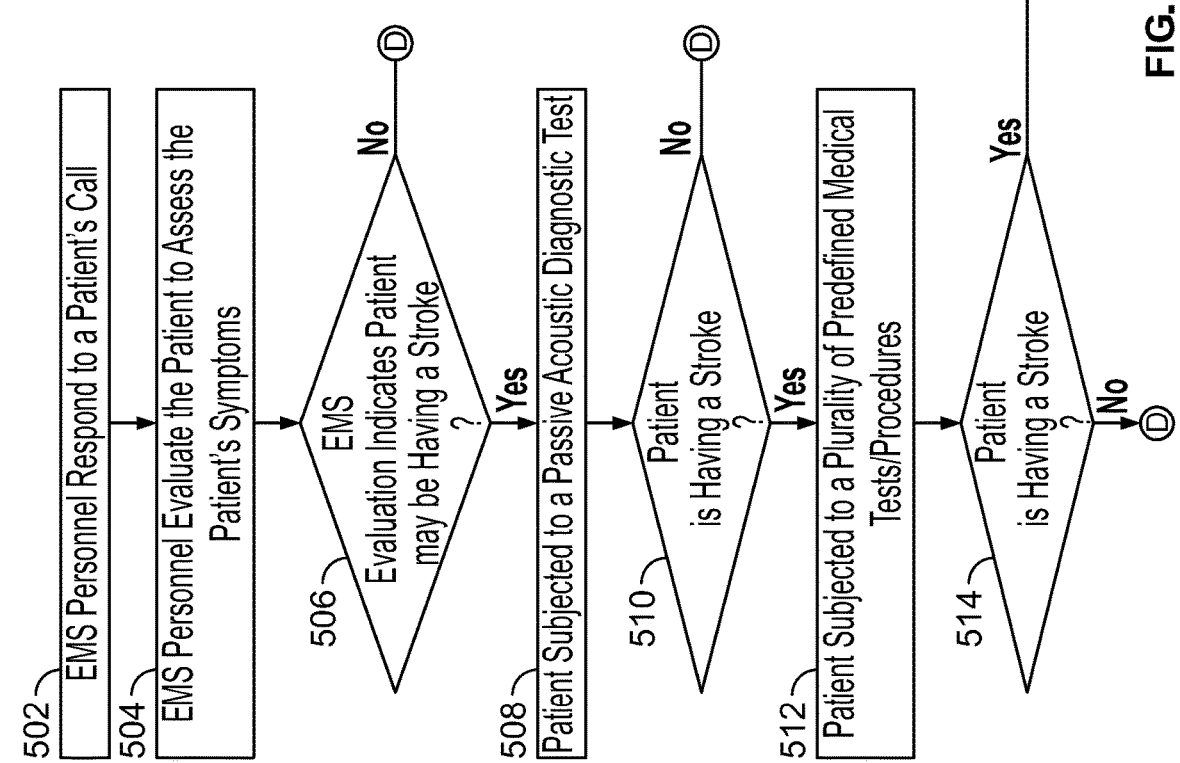
Figure 6A:
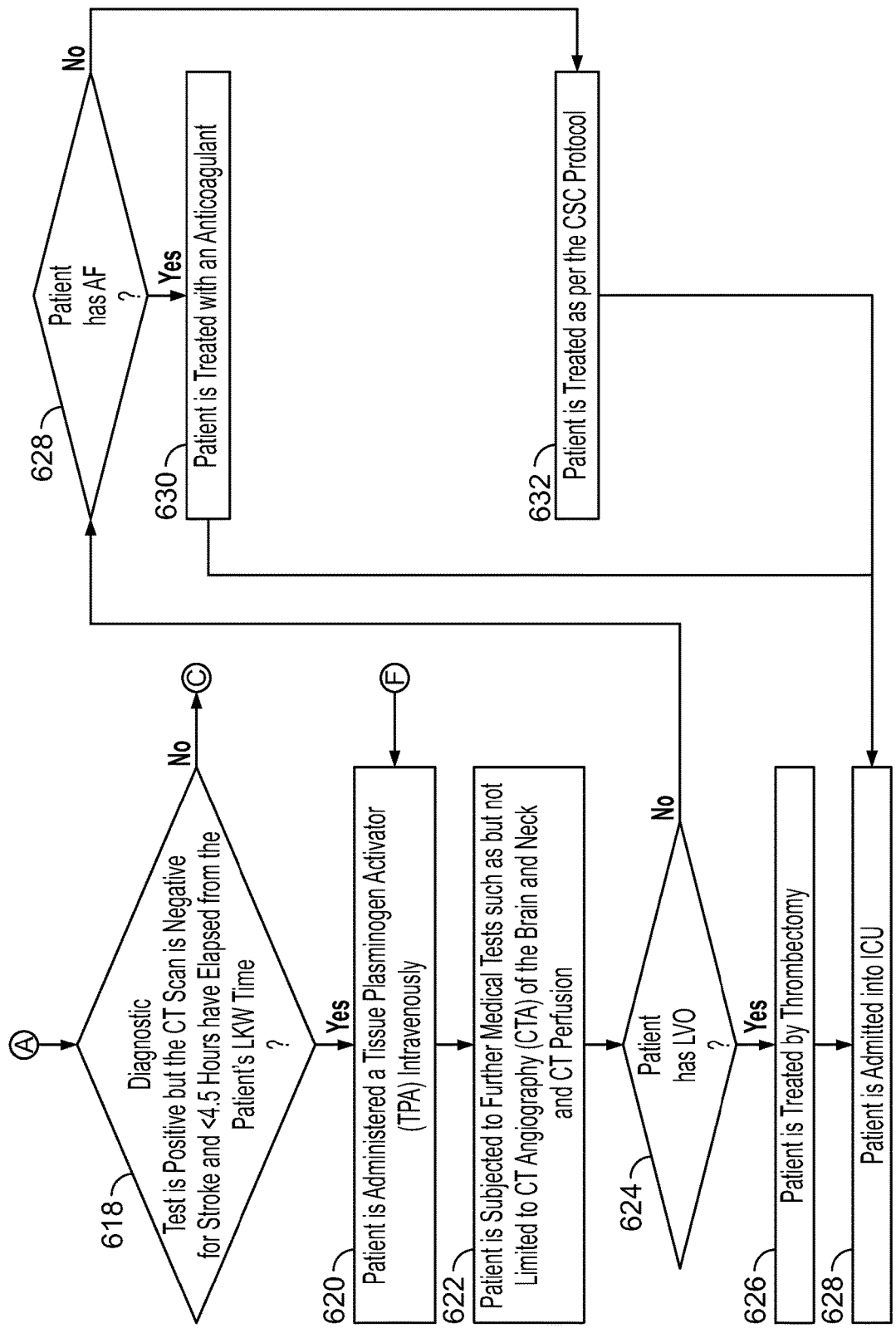
FIG. 6A is a flowchart illustrating a method of responding to a patient presenting with complaints of stroke or migraine by a comprehensive stroke center (CSC), in accordance with an embodiment of the present specification.
Figure 6A:
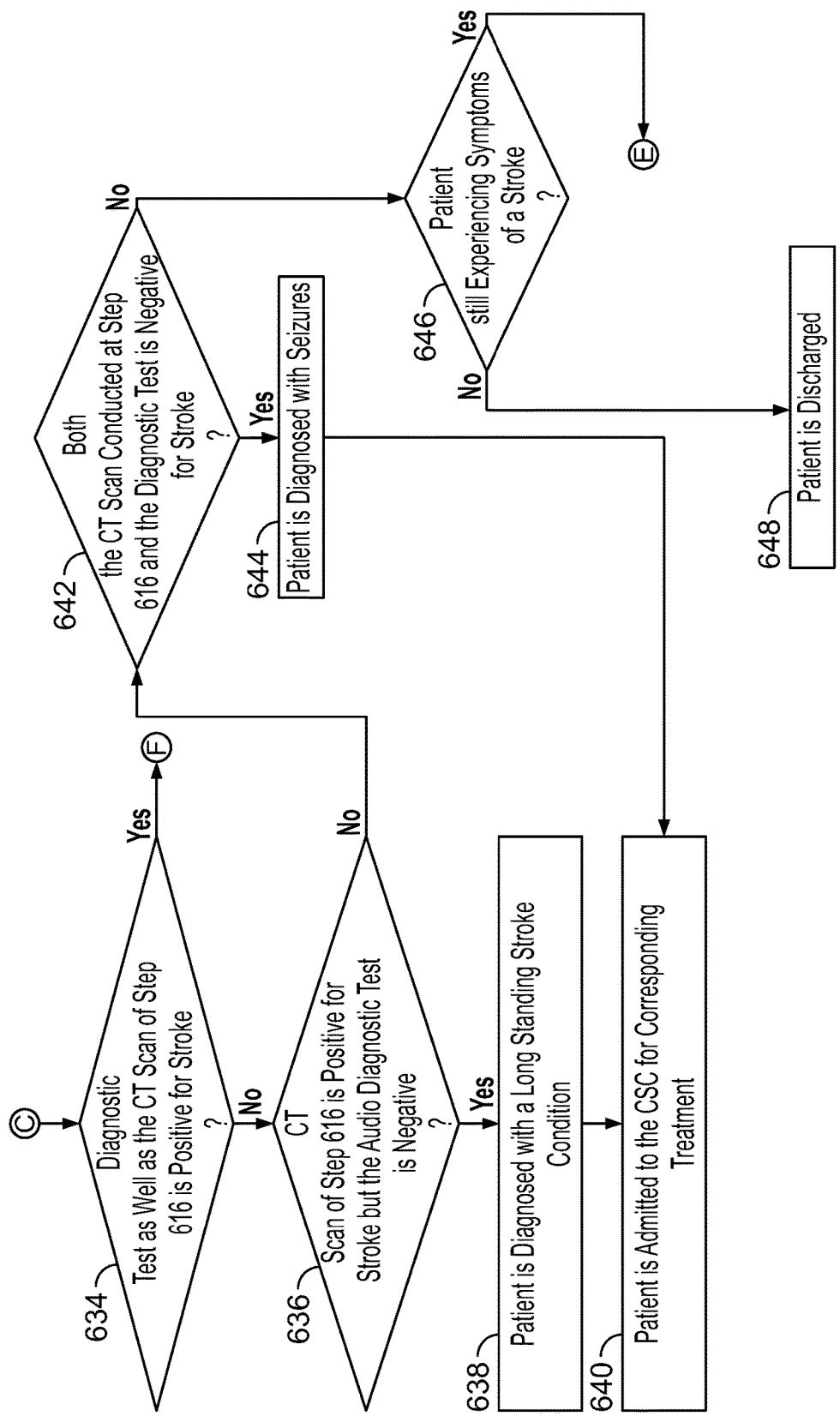

Thereafter, the assessment application automatically takes an EMS personnel through a first plurality of assessment/screening steps of FIG. 5A and a CSC personnel through a second plurality of assessment/screening steps of FIG. 6A. Subsequently, the assessment application provides the EMS and CSC personnel with results of the assessment or screening steps at the end of a predefined period of time (say, for example, 2 minutes). Thus, the assessment application is configured to guide the medical personnel through a decision tree based on clinical findings and results of the passive acoustic diagnostic test using the headset.

FIG. 5A is a flowchart illustrating a method of responding to a patient presenting with complaints of stroke or migraine by Emergency Medical Services (EMS), in accordance with an embodiment of the present specification.

At step 502, EMS personnel responds to a patient call. In embodiments, the patient calls a central EMS number for requesting help with respect to symptoms of stroke or migraine.

At step 504, the EMS personnel acquires a plurality of patient data in order to assess or evaluate the patient's symptoms. In some embodiments, in response to the patient's call, the EMS personnel executes the assessment application on his user device that enables the medical personnel to sign in with his unique ID, and implement a triage process that directs the EMS personnel through a plurality of GUIs, in order to assess if the patient is suffering from LVO/stroke or migraine. In embodiments, each of the plurality of GUIs presents a plurality of input prompts to acquire clinical/medical data relevant to determining a stroke (and specifically a LVO).

Figure 5C:
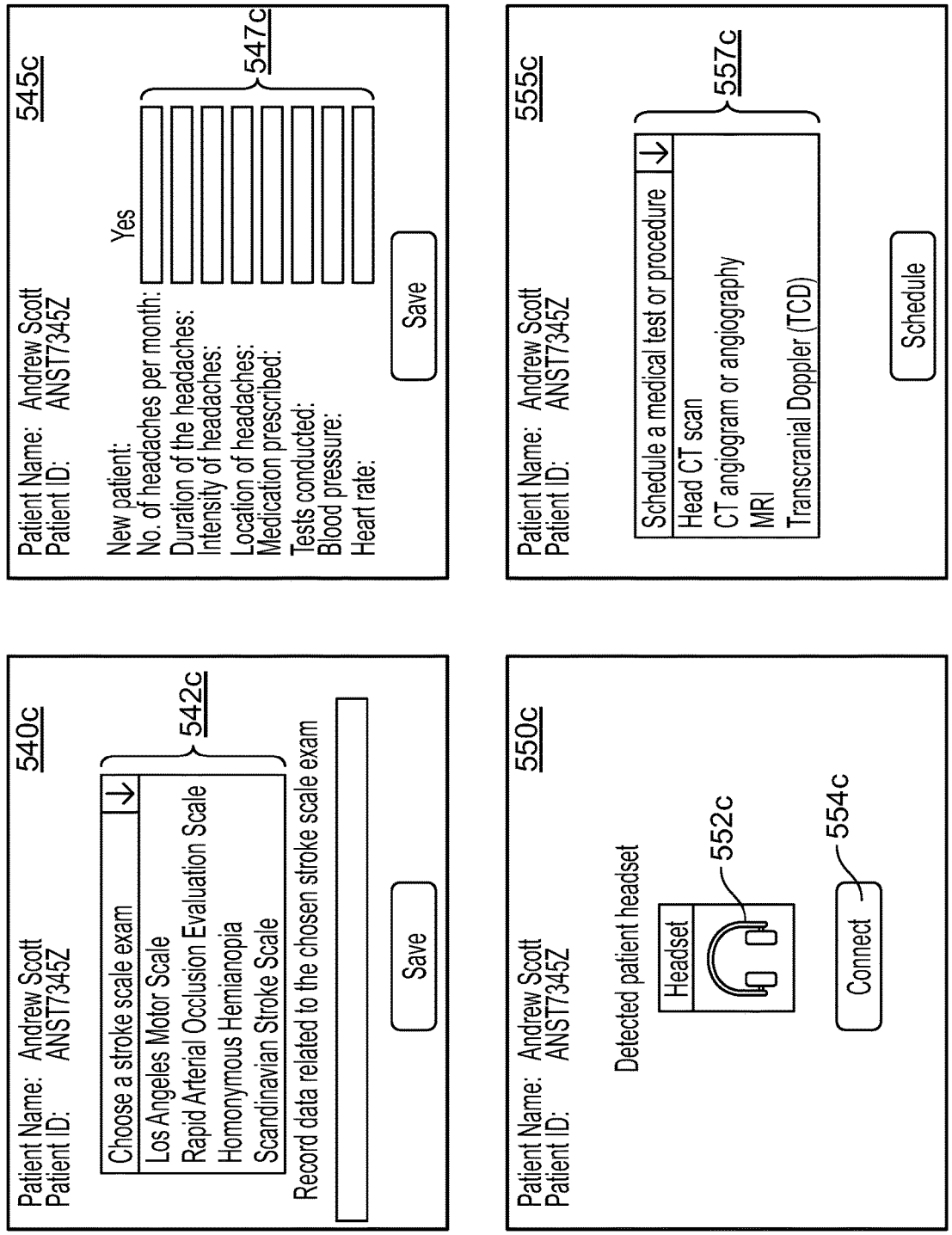
FIG. 5C illustrates a plurality of exemplary GUIs (Graphical User Interfaces) generated by an assessment application in the context of the method of FIG. 5A, in accordance with some embodiments of the present specification.

In some embodiments, as shown in FIG. 5C, the assessment application generates a GUI 540c to enable the EMS personnel to acquire patient's data in accordance with standard predefined stroke assessment protocols. In an embodiment, the GUI 540c prompts the EMS personnel to acquire data corresponding to one or more of a plurality of stroke scale exams 542c to identify if the patient is having a stroke and to determine the severity of the stroke. In embodiments, the plurality of stroke scale exams 542c include tests such as, but not limited to, the Los Angeles Motor Scale (LAMS), the Rapid Arterial Occlusion Evaluation (RACE) scale, Cincinnati Prehospital Stroke Scale (CPSS), NIHSS (National Institutes of Health Stroke Scale), Homonymous Hemianopia (H&H), Scandinavian Stroke Scale (SSS), FAST (Face Arm Speech Test), Los Angeles Prehospital Stroke Screen (LAPSS), CNS (Canadian Neurological Scale), Minor Stroke Syndrome (MSS), Cincinnati Stroke Triage Assessment Tool (C-STAT), Vision, Aphasia, or Neglect (VAN), ABCD$^2$ (Age, Blood Pressure, Clinical Features, Duration of TIA and presence of diabetes), European Stroke Scale (ESS), OSS, Field Assessment Stroke Triage for Emergency Destination (FAST-ED), NIH Stroke Scale (NIHSS), Glasgow Coma Scale (GCS), Oxfordshire Community Stroke Project Classification (OCSPC), Postural Assessment Scale for Stroke (PASS). For example, VAN is used for testing the vision of the patient. It is tested if the patient can see in right, left, up and down directions, if the patient exhibits aphasia and can understand and produce language, and if the patient exhibits neglect and looks only at one side ignoring the other side. However, the accuracy with which these tests determine the occurrence of a stroke ranges from 50 to 70%. If a patient having a stroke is misdiagnosed, the patient may suffer one or more permanent disability, become medically dependent, require rehabilitation, or experience hemorrhagic complications that may lead to death.

In some embodiments, the assessment application generates at least one other GUI 545c to enable the EMS personnel to acquire additional patient data 547c related to aspects such as, but not limited to, whether the patient is new or a returning patient, number of headaches experienced each month, duration of the headaches, list of medication prescribed, intensity of the headaches or pain level, specific site or location of the headaches, tests performed (for example, MRI, CT, etc.), blood pressure measurements, and/or pulse rate.

At step 506 it is determined if the EMS evaluation indicates that the patient may be having a stroke. Specifically, the assessment application optimizes the AI algorithms to process the acquired plurality of patient data in order to first determine if the patient is suffering from a stroke (LVO) relative to any other condition.

Based on the evaluation at step 506 if the patient is suspected of having a stroke then, at step 508, the patient is subjected to an acoustic diagnostic test. In embodiments, the acoustic diagnostic test comprises providing the patient with a headset and synchronizing, pairing or connecting the assessment application with the headset. As shown in FIG. 5C, the assessment application generates a GUI 550c prompting the EMS personnel to synchronize, pair or connect the application with the patient's headset 552c. The application automatically detects the patient's headset 552c and synchronizes, pairs or connects with the detected headset 552c when the EMS personnel actuates the 'connect' icon 554c. The headset is configured to passively detect the vibration of a fluid or elastic solid, generated from the cardiac cycle of the patient such as is described with reference to FIGS. 1C, 1D and 2. In embodiments, the headset may be configured to passively detect acoustic frequencies. In various embodiments, the detected vibrations are compared with a predefined set of pre-recorded vibrations for determining whether the detected vibrations from the patient correspond to any of a plurality of medical conditions/pathologies such as, but not limited to, large vessel occlusion (LVO) and migraines.

The method of determining if the patient is suffering from a pathology, in accordance with some embodiments of the present specification is described with reference to FIGS. 3 and 4A above. As explained with reference to FIG. 4A, the detected vibrations received from each microphone of the headset are processed, the processed data is used to obtain a spectrogram comprising a unique pattern and indicating an exclusive signature for a pathology, and the obtained spectrogram is compared with a spectrogram obtained by using pre-recorded vibrations of a healthy human having no pathologies, as well as with a plurality of pre-recorded spectrograms for determining if any of a set of pre-defined pathologies are present in the patient's acoustic data, in order to determine if the patient suffers from any of the plurality of pre-defined pathologies.

In an embodiment, the spectrogram of a patient suffering from LVO/stroke comprises one or more low and mid-frequency reflection. The spectrogram may also comprise some echo of the systolic rhythm of the patient, as the patient's blood vessels are blocked, the pressure of blood being pumped into the blocked vessels may result in a rigid expansion and then loosening of the vessel walls with each heartbeat. In an embodiment, this results in the patient's spectrogram being spread-out temporally (in the time direction), with the systolic and diastolic signals shifted up (in the frequency direction) since a blocked vessel is more rigid under higher pressure, as compared to a healthy (not suffering from LVO) person's spectrogram.

FIG. 5B illustrates a spectrogram of a healthy person compared with a spectrogram of a patient suffering from a stroke, in accordance with an embodiment of the present specification. As shown in the Figure, spectrogram 540 of a healthy person corresponds to an EKG result 542, and a diastole and systole graph 546 of the healthy person. Spectrogram 544 represents data of a person suffering from a stroke. Upon comparing spectrogram 544 with the spectrogram 540 it can be observed that distance between top of systole peak 548 to average top of diastole peak 550 in spectrogram 544 of a stroke patient, is less than the distance between systole peak 552 and diastole peak 554 in the spectrogram 540 of a healthy person, as the diastole peaks 550 are higher than the healthy person's diastole peaks 554. Further, an abnormal presence of double systole peaks 556, 548 can be seen in spectrogram 544. Also, the systole peaks 548 are wider than systole peak 552 of a healthy person.

At step 510 it is determined by using the acoustic diagnostic test if the patient is having a stroke. In some embodiments, the assessment application is configured to acquire audio data corresponding to the acoustic diagnostic test, upload the audio data to a cloud processing platform, receive a result from the cloud processing platform indicative of whether the patient is having a stroke or not and display the result on the EMS personnel's device.

At step 510, if it is determined by the acoustic diagnostic test that the patient is having a stroke then, at step 512, the patient is subjected to a plurality of predefined medical tests/procedures that are part of a standard medical stroke protocol. As shown in FIG. 5C, the assessment application generates a GUI 555c that prompts the EMS personnel to select and schedule at least one of a plurality of predefined medical tests/procedures 557c. In an embodiment, the plurality of predefined medical tests/procedures 557c include tests such as, but not limited to, a CT (Computerized Tomography) scan of the head, a CT angiogram or angiography, MRI, and TCD (Transcranial Doppler).

At step 514 it is again determined if the patient is suspected of suffering from a stroke based on the results of the tests conducted at step 512 (and input into the assessment application via at least one GUI). At step 514 if it is determined that the patient is suspected of suffering from a stroke, then at step 516 it is determined by the assessment application if less than 6 hours have elapsed from the patient's last know well (LKW) time. At step 518, if less than 6 hours have elapsed from the patient's LKW time, based on direction by the assessment application, the patient is transferred to a stroke care facility as per the patient's insurance policy. At step 520, if more than 6 hours have elapsed from the patient's LKW time, the patient is transported to the nearest comprehensive stroke center (CSC) for treatment based on a recommendation by the assessment application.

At steps 506, 510 and 514 if it is determined that the patient is not suspected of suffering from a stroke, the assessment application goes on to evaluate if the patient is instead suffering from migraine and the method flow moves to step 522. Accordingly, at step 522 it is determined if the patient may be suffering from migraine. Specifically, in some embodiments, the assessment application is programmed to automatically subject patient data, acquired earlier at step 504, to AI algorithms optimized for determining migraine. Alternatively, the assessment application may prompt the EMS personnel to re-acquire patient data in case the earlier patient data (acquired at step 504) is not sufficient for determining a migraine.

If it is determined, at step 522, that the patient is likely suffering from migraine then, at step 524, the assessment application directs the EMS personnel to subject the patient to an acoustic diagnostic test for diagnosing migraine. At step 526 if it is determined by the acoustic diagnostic test that the patient is suffering from migraine, then at step 528 the patient is diagnosed and treated for migraine. In some embodiments, if the acoustic diagnostic test determines that the patient is not suffering from migraine, however the EMS personnel is not satisfied with the test result, the patient may be subjected to the acoustic test for diagnosing migraine for a second time for re-evaluation of the patient's symptoms. If the patient is not suffering from migraine as determined at steps 522, 526 then the patient is transferred to a hospital for further diagnosis and treatment.

FIG. 6A is a flowchart illustrating a method of responding to a patient presenting with complaints of stroke or migraine by comprehensive stroke center (CSC), in accordance with an embodiment of the present specification. At step 602 a patient presenting with symptoms of a stroke is admitted to a CSC. In embodiments, the patient has been administered one or more of the predefined stroke screenings and has been diagnosed as suffering from an LVO/stroke by EMS, before being admitted to the CSC. The tests/screenings conducted by EMS show the progression of the disease either improving or worsening and allows clinicians to follow the disease process and set up treatment/therapy regime based on dynamic changes. In some embodiments, a CSC personnel signs-in (using his unique ID) to the assessment application on his user device and, based on inputting the patient's ID, for example, is authorized to access various patient data acquired and results of tests/screening conducted by EMS (as described with reference to FIG. 5A).

At step 604 the patient is subjected to one or more predefined medical tests in accordance with standard CSC protocol and is administered fluids via an intravenous (IV) line. In some embodiments, the assessment application generates at least one GUI to direct the CSC personnel to subject the patient to one or more predefined medical tests. In an embodiment, the patient is subjected to blood tests such as but not limited to: CBC, CMP, COAGS); drug screening, urinalysis, CXR, EKG, CT Head, CTA, MRI Brain, MRA, CT Perfusion, TCD, and EEG. Data corresponding to the tests is provided to the assessment application via inputs through at least one GUI or alternatively communicated directly to the assessment application (if authorized by the patient) from the test laboratories.

At step 606 the patient is subjected to the acoustic diagnostic test for diagnosing stroke, in accordance with an embodiment of the present specification. In embodiments, the acoustic diagnostic test comprises providing the patient with a headset and synchronizing, pairing or connecting the assessment application with the headset. In some embodiments, the assessment application generates a GUI prompting the CSC personnel to synchronize, pair or connect the application with the patient's headset. In some embodiments, the assessment application is configured to acquire audio data corresponding to the acoustic diagnostic test, upload the audio data to a cloud processing platform and receive a result from the cloud processing platform indicating whether the patient is suffering from a stroke or not.

At step 608, the patient undergoes a brain non-contrast computer tomography (CT) scan. In some embodiments, results of the CT scan are provided to the assessment application via inputs through at least one GUI or alternatively communicated directly to the assessment application (if authorized by the patient) from the test laboratory.

At step 610 it is determined if the patient is suffering from a hemorrhage based on the conducted tests. As shown in FIG. 6B, the assessment application generates a GUI 660 displaying various patient data 662 that is being processed to determine if the patient is suffering from a hemorrhage. In some embodiments, the assessment application uses patient data 622 including a) first data acquired and results of tests/screening conducted by EMS in FIG. 5A, b) second data corresponding to tests conducted at step 604, c) third data corresponding to acoustic diagnostic test conducted at step 606 and/or d) fourth data corresponding to the brain non-contrast CT scan of step 608.

If the patient is suffering from a hemorrhage, then at step 612 it is determined if the patient has a high blood pressure (BP). As shown in FIG. 6B, the assessment application generates a GUI 665 that provides areas 667 for the CSC personnel to input most recent BP values of the patient. At step 614 the patient, if diagnosed as having a hemorrhage and high BP, undergoes one or more medical procedures such as, but not limited to, clipping/coiling of aneurism or other surgery as per the standard predefined protocol. In embodiments, the assessment application recommends the one or more medical procedures. At step 616, after the medical procedure the patient is admitted into an intensive care unit (ICU) of the CSC.

At step 618 it is determined if the audio diagnostic test is positive for stroke but the CT scan results do not show that the patient is having a stroke and less than four and a half hours have elapsed from the patient's LKW time. In embodiments, the audio diagnostic test uses auditory patterns in the cerebral vasculature of the patient caused due to blocked blood vessels and compares them to pre-recorded patterns of patient's suffering from a stroke, for determining if the patient is positive for stroke. As shown in FIG. 6B, the assessment application generates a GUI 670 displaying, for example, that the audio diagnostic test 671 is positive for stroke, the CT scan results 672 are negative for a stroke and less than four and a half hours 673 have elapsed from the patient's LKW time.

At step 620 if the audio diagnostic test is positive for stroke but the CT scan is negative, the patient is administered a tissue plasminogen activator (TPA) intravenously. As shown in FIG. 6B, the assessment application generates a GUI 675 with a prompt 677 (when the CSC personnel actuates the 'next step' icon 674 of GUI 670) directing the CSC personnel to administer TPA intravenously to the patient. In embodiments, the result of a CT scan is used to rule out a hemorrhage in the patient. A negative CT indicates that there is no quantification or scoring. The standard Alberta Stroke Program Early CT Score (ASPECTS) scoring measures a completed stroke infarct and provides quantitative measure of stroke burden on the brain.

At step 621 the patient is subjected to further medical tests such as but not limited to CT angiography (CTA) of the brain and neck and CT perfusion (CTP). As shown in FIG. 6B, the assessment application generates a GUI 680 with a prompt 682 directing the CSC personnel to subject the patient to additional medical tests. In an embodiment, the acoustic diagnostic test is validated by a CTA test to provide objective data. In an embodiment, the test may provide a binary result, while in another embodiment, the test provides results represented on a scale based on intensity. In an embodiment, where a patient's artery is completely occluded, the test would yield a binary result.

In an embodiment, positive findings of a CT scan, a CTA, and a CTP imply a positive finding of a completed stroke test and precludes acute interventions such as thrombolytic, or mechanical thrombectomy. Positive findings of a CT scan, and a CTP with a negative finding of a CTA may, in an embodiment, indicate including intervention such as thrombectomy to treat the patient, and may also indicate the need for further aggressive interventions. In an embodiment, positive findings of a CT scan with a negative finding of a CTA and CTP may indicate the absence of a stroke and the patient may require medical interventions only and further tests such as but not limited to, MM, DWI, IF and TPA. In an embodiment, positive findings of a CT scan and a CTA with a negative finding of a CTP may indicate an old stroke and no intervention may be needed. In an embodiment, positive findings of a CT scan, CTA, CTP, Rapid processing of perfusion and diffusion (RAPID) and ASPECTS score may indicate the need for a thrombectomy and further medical interventions. In an embodiment, positive findings of a CT scan and a CTA with a negative finding of a CTP along with no intervention may lead to a need for aggressive medical/ICU management, primarily fluid support and close observation. In various embodiments, multiple other case scenarios may emerge with the patient being tested via CT scan, CTA, CTP and other such tests.

At step 622 it is determined, by the assessment application in data communication with a cloud computing platform, based on the conducted medical tests at step 621 if the patient has LVO, in which case at step 624 the patient is subjected to a thrombectomy and is admitted into an intensive care unit (ICU) of the CSC at step 626. In some embodiments, the assessment application prompts and directs the CSC personnel to subject the patient to a thrombectomy procedure.

At step 628 it is determined, by the assessment application in data communication with a cloud computing platform, based on the passive acoustic diagnostic test conducted at step 606 if the patient has atrial fibrillation (AF) in which case at step 630 the patient is treated with an anticoagulant and is admitted into an intensive care unit (ICU) of the CSC (as shown by the flow moving from step 630 back to step 626). The passive acoustic diagnostic test detects irregular heart rate caused due to AF and thus enables diagnosis of AF. In some embodiments, the assessment application prompts and directs the CSC personnel to treat the patient with an anticoagulant and admit the patient to an ICU of the CSC.

If it is determined at step 622 that the patient does not have LVO and at step 628 that the patient also does not have AF, then at step 632 the assessment module generates prompts to direct the CSC personnel to treat the patient as per predefined medical protocols based on a plurality of pre-recorded causes of the patient's symptoms and the patient is admitted into an intensive care unit (ICU) of the CSC for further monitoring (as shown by the flow moving from step 632 back to step 626). In embodiments the patient in the ICU is subjected to close serial neurologic observation, fluid support, BP management, further imaging (CT, Mill, carotid ultrasound) and serial blood tests.

If the condition determined at step 618 is false, then at step 634 it is determined, by the assessment application in data communication with the cloud processing platform, if the audio diagnostic test as well as the CT scan is positive for stroke, in which case steps 620 to 626 are repeated. If the conditioned determined at step 634 is false, it is determined, by the assessment application in data communication with the cloud processing platform, at step 636 if the CT scan conducted at step 616 is positive for stroke but the audio diagnostic test is negative, in which case at step 638 the patient is diagnosed with a long standing stroke condition and is admitted to the CSC for corresponding treatment at step 640. In an embodiment, the patient is subjected to an Mill test and/or CT test for diagnosing that the patient with a long standing stroke condition. A CT/MRI test confirms the acuity or chronicity of a stroke. In embodiments, the assessment application generates prompts to direct the CSC personnel through steps 638 and 640.

If the condition determined at step 636 is negative it is determined, by the assessment application in data communication with the cloud processing platform, at step 642 if both the CT scan conducted at step 616 and the audio diagnostic test is negative for stroke, which if true, the patient is diagnosed with seizures at step 644 and is admitted to the CSC for corresponding treatment. In an embodiment, the patient is subjected to an EEG for diagnosing that the patient is having seizures. In an embodiment if the condition determined at step 642 is negative, it is determined if the patient is still suffering from stroke like symptoms at step 646, which if true steps 604 onwards are repeated, else the patient is discharged from the CSC at step 648. In embodiments, the assessment application generates prompts to direct the CSC personnel through steps 644, 646 and 648.

In various embodiments, a patient diagnosed with a stroke condition as per the steps described in FIGS. 5A and 6A above, once admitted into an ICU, is constantly monitored and is subjected to a plurality of predefined treatment regimes. In embodiments, for a patient admitted to an ICU with a hemorrhagic stroke diagnosis, BP, neurological functions and ICP are measured every two hours and the patient is subjected to the acoustic diagnostic test for strokes every fifteen minutes. In embodiments, for a patient admitted to an ICU with a non-hemorrhagic stroke diagnosis, temperature and pain level is monitored every eight hours, while a complete blood count and electrolytes of the patient are measured daily; and the patient is subjected to the acoustic diagnostic test for strokes every hour. In embodiments, the results of the acoustic diagnostic test enable the medical personnel treating the patient, to diagnose a stroke condition and treat the patient accordingly.

The diagnostic system and method of the present specification provides numerous benefits and advantages over known stroke assessment approaches. In embodiments, the specification utilizes a passive microphone approach that analyzes signals by an algorithm and classifies them, which allows an objective detection of strokes (both ischemic and hemorrhagic), non-invasively. Moreover, the low cost non-invasive, acoustic based approach does not interrupt a standard stroke handling protocol, but instead aids in quick and decisive diagnosis, at times, without the need of time consuming invasive medical procedures, therefore, enhancing the processes of screening, diagnosis and prescription of drug appropriate forms of therapy. Furthermore, the diagnostic system and method of the present specification can detect a normal condition (not suffering from a stroke) from an ischemic stroke or migraine; an ischemic stroke from hemorrhagic stroke and, an LVO from an AF and other similar brain conditions.

The above examples are merely illustrative of the many applications of the system and method of present specification. Although only a few embodiments of the present specification have been described herein, it should be understood that the present specification might be embodied in many other specific forms without departing from the spirit or scope of the specification. Therefore, the present examples and embodiments are to be considered as illustrative and not restrictive, and the specification may be modified within the scope of the appended claims.

We claim:
1. A diagnostic system for triaging a patient suffering from a brain condition, the system comprising:
 a head worn device comprising at least one acoustic sensor configured to detect vibrations generated by a cerebral vasculature of the patient's brain;

a software program configured to execute on a mobile computing device, wherein, when executed, the software program is configured to:
  present a plurality of graphical user interfaces configured to direct a user through a triaging process for the patient;
  receive data indicative of the detected vibrations; and
  process the data to obtain at least one signal; and
a signal analyzer coupled with the software program and configured to analyze the at least one signal to identify a pattern indicative of a large vessel occlusion.

2. The diagnostic system of claim 1, wherein the signal analyzer is optimized to identify a large vessel occlusion relative to any other brain condition.

3. The diagnostic system of claim 1, wherein the pattern indicative of a large vessel occlusion is defined, at least in part, by a difference between a maximum height of a systole peak in the at least one signal to a maximum height of a diastole peak adjacent to the systole peak in the at least one signal being less than a difference between a maximum height of a systole peak and a maximum height of an adjacent diastole peak in a reference signal.

4. The diagnostic system of claim 1, wherein the pattern indicative of a large vessel occlusion is defined, at least in part, by a greater number of double systole peaks in the at least one signal relative to a reference signal, wherein a double systole peak is defined as a temporal sequence of a first systole peak, a first valley, a second systole peak, a second valley, and a diastole peak and wherein the reference signal is a signal derived from received vibrations of a person who does not have a large vessel occlusion.

5. The diagnostic system of claim 1, wherein the pattern indicative of a large vessel occlusion is defined, at least in part, by a ratio of a maximum height of a systole peak in the at least one signal relative to a minimum height of a valley adjacent to the systole peak being less than a ratio of a maximum height of a systole peak in a reference signal relative to a minimum height of a valley adjacent to the systole peak in the reference signal and wherein the reference signal is a signal derived from received vibrations of a person who does not have a large vessel occlusion.

6. The diagnostic system of claim 1, wherein at least one of the plurality of graphical user interfaces prompts the user for data indicative of a CT scan of the patient's brain.

7. The diagnostic system of claim 1, wherein at least one of the plurality of graphical user interfaces prompts the user for data indicative of a stroke scale exam.

8. The diagnostic system of claim 1, wherein at least one of the plurality of graphical user interfaces prompts the user for data indicative of whether the patient suffers from a hemorrhage.

9. The diagnostic system of claim 1, wherein at least one of the plurality of graphical user interfaces prompts the user for data indicative of at least one of the patient's heart rate or blood pressure.

10. The diagnostic system of claim 1, wherein, if a large vessel occlusion is not identified, the signal analyzer is further configured to analyze the at least one signal to identify a pattern indicative of a migraine.

11. The diagnostic system of claim 1, wherein, if a large vessel occlusion is not identified, the software program is further configured to activate the head worn device to detect a second set of vibrations generated by the cerebral vasculature of the patient's brain, receive data indicative of the second set of detected vibrations from the head worn device, and process the data indicative of the second set of detected vibrations to obtain a second signal.

12. The diagnostic system of claim 11, wherein the signal analyzer is further configured to analyze the second signal to identify a pattern indicative of a migraine.

13. The diagnostic system of claim 1, wherein the software program is further configured to process at least one of imaging data or physical exam data together with the identified pattern to generate a determination of whether the patient is undergoing a stroke and to display the determination in at least one of the plurality of graphical user interfaces.

14. The diagnostic system of claim 1, wherein the software program is further configured to display, in at least one of the plurality of graphical user interfaces, a first recommendation if at least one of imaging data or physical exam data indicates the patient is having a stroke and if the identified pattern does not indicate the patient is having a stroke.

15. The diagnostic system of claim 14, wherein the software program is further configured to display, in at least one of the plurality of graphical user interfaces, a second recommendation if at least one of imaging data or physical exam data indicates the patient is having a stroke and if the identified pattern also indicates the patient is having a stroke, wherein the first recommendation is different from the second recommendation.

16. A system for diagnosing a patient suffering from a brain condition, the system comprising:
  a head worn device comprising at least one acoustic sensor configured to detect vibrations generated by a cerebral vasculature of the patient's brain;
  a software program configured to execute on a mobile computing device, wherein, when executed, the software program is configured to:
  receive at least one of blood work data, historical treatment data, physical exam data, or imaging data of the patient;
  receive data indicative of the detected vibrations; and
  process the data indicative of the detected vibrations to obtain at least one signal; and
  a signal analyzer coupled with the software program and configured to analyze the at least one signal to identify a pattern indicative of at least one of a large vessel occlusion, stroke, or migraine, wherein the software program is configured to process the at least one of blood work data, physical exam data, historical treatment data or imaging data together with the identified pattern to generate a diagnosis of the patient and is configured to display the generated diagnosis in at least one graphical user interface, and wherein the diagnosis indicates whether the patient is suffering from at least one of a large vessel occlusion, stroke or migraine.

17. The system of claim 16, wherein the pattern indicative of a large vessel occlusion is defined, at least in part, by a difference between a maximum height of a systole peak in the at least one signal to a maximum height of a diastole peak adjacent to the systole peak in the at least one signal being less than a difference between a maximum height of a systole peak and a maximum height of an adjacent diastole peak in a reference signal.

18. The system of claim 16, wherein the pattern indicative of a large vessel occlusion is defined, at least in part, by a greater number of double systole peaks in the at least one signal relative to a reference signal, wherein a double systole peak is defined as a temporal sequence of a first systole peak, a first valley, a second systole peak, a second valley, and a diastole peak and wherein the reference signal is a signal derived from received vibrations of a person who does not have a large vessel occlusion.

19. The system of claim 16, wherein the pattern indicative of a large vessel occlusion is defined, at least in part, by a ratio of a maximum height of a systole peak in the at least one signal relative to a minimum height of a valley adjacent to the systole peak being less than a ratio of a maximum height of a systole peak in a reference signal relative to a minimum height of a valley adjacent to the systole peak in the reference signal and wherein the reference signal is a signal derived from received vibrations of a person who does not have a large vessel occlusion.

20. The system of claim 16, wherein the signal analyzer is optimized to first identify a large vessel occlusion relative to a migraine.

* * * * *